US006184369B1

(12) United States Patent
Rando et al.

(10) Patent No.: US 6,184,369 B1
(45) Date of Patent: *Feb. 6, 2001

(54) ANTI-VIRAL GUANOSINE-RICH OLIGONUCLEOTIDES

(75) Inventors: Robert F. Rando; Susan Fennewald; Joseph G. Zendegui, all of The Woodlands; Joshua O. Oiwana, Spring; Michael E. Hogan, The Woodlands, all of TX (US)

(73) Assignee: Aronex Pharmaceuticals, Inc., The Woodlands, TX (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/535,168

(22) PCT Filed: Apr. 25, 1994

(86) PCT No.: PCT/US94/04529

§ 371 Date: Oct. 23, 1995

§ 102(e) Date: Oct. 23, 1995

(87) PCT Pub. No.: WO94/25037

PCT Pub. Date: Nov. 10, 1994

Related U.S. Application Data

(63) Continuation-in-part of application No. 08/145,704, filed on Oct. 28, 1993, now Pat. No. 5,567,604, which is a continuation-in-part of application No. 08/053,027, filed on Apr. 23, 1993, now abandoned, which is a continuation-in-part of application No. 08/145,704, filed on Oct. 28, 1993, now Pat. No. 5,567,604, and a continuation-in-part of application No. 08/053,027, filed on Apr. 23, 1993, now abandoned.

(51) Int. Cl.$^7$ .......................... C07H 21/00; C07H 21/02; C07H 21/04
(52) U.S. Cl. ..................... 536/23.1; 536/24.5; 536/25.5; 514/44; 435/6
(58) Field of Search ................................ 536/23.1, 24.5; 536/25.5; 514/44

(56) References Cited

U.S. PATENT DOCUMENTS

| | | | |
|---|---|---|---|
| 3,687,808 | * | 8/1972 | Merigan et al. ................. 536/23.1 |
| 4,388,306 | * | 6/1983 | Field et al. ....................... 424/177 |
| 4,981,957 | * | 1/1991 | LeBleu et al. ................... 536/25.2 |
| 5,075,217 | * | 12/1991 | Weber ................................... 435/6 |
| 5,176,996 | * | 1/1993 | Hogan et al. ........................ 435/6 |
| 5,334,711 | * | 8/1994 | Sproat et al. .................... 536/24.5 |
| 5,397,702 | * | 3/1995 | Cahalan et al. ................. 435/69.1 |
| 5,428,007 | * | 6/1995 | Fischer et al. ....................... 514/6 |
| 5,567,604 | | 10/1996 | Rando et al. ..................... 435/238 |
| 5,591,721 | | 1/1997 | Agrawal et al. .................... 514/44 |

FOREIGN PATENT DOCUMENTS

| | | |
|---|---|---|
| 0375408 | 6/1990 | (EP) . |
| 0713705A | 5/1996 | (EP) . |
| 8901036 | * 2/1989 | (WO) . |
| WO9408053 | 4/1994 | (WO) . |

OTHER PUBLICATIONS

He et al., "Characterization of Human Cytomegalovirus UL84 Early Gene and Identification of Its Putative Protein Product," *J. Virology*, 66(2), 1098–1108 (1992).*

Oram et al., "Use of Recombinant Plasmids to Investigate the Structure of the Human Cytomegalovirus Genome," *J. Gen. Virology*, 59, 111–129 (1982).*

Weston et al., "Sequence of the Short Unique Region, Short Repeats, and art of theLong Repeats of Human Cytomegalovirus," *J. Mol. Biology*, 192, 177–208 (1986).*

Tamashiro et al.(I), "Structure of the Heterogeneous L–S Junction Region of Human Cytomegalovirus Strain AD169 DNA," *J. Virology*, 52(2), 541–548 (1984).*

Mocarski et al., "Structure and Variability of the a Sequence in the Genome of Human Cytomegalovirus (Towne Strain)," *J. Gen.Virology*, 68, 2223–2230 (1987).*

Tamashiro et al.(II), "Terminal Structure and Heterogeneity in Human Cytomegalovirus Strain AD 169," *J. Virology*, 59(3), 591–604 (1986).*

Hennighausen et al., "Nuclear Factor 1 Interacts with Five DNA Elements int eh Promoter Region of the Human Cytomegalovirus Major Immediate Early Gene," *EMBO J.*, 5(6), 1367–1371 (1986).*

Rasmussen et al., "Sequences in Human Cytomegalovirus Which Hybridize with the Avian Retrovirus Oncongene v–myc Are G+C Rich and Do Not Hybridize with the Human c–myc Gene," *Molecular & Cellular Biology*, 5(6), 1525–1530 (1985).*

G. Zon, "Oligonucleotide Analogues as Potential Chemotherapeutic Agents," *Pharmaceutical Research*, 5(9), 539–549 (1988).*

Miller et al., "Control of Ribonucleic Acid Function by Oligonucleoside Methylphosphonates," *Biochemie*, 67, 769–776 (1985).*

Marshall et al., "Phosphorodithioate DNA as a Potential Therapeutic Drug," *Science*, 259, 1564–1570 (1993).*

(List continued on next page.)

*Primary Examiner*—Douglas W. Robinson
*Assistant Examiner*—Eric Crane
(74) *Attorney, Agent, or Firm*—McDaniel & Associates

(57) ABSTRACT

The oligonucleotides have sufficient guanosine to form a guanosine tetrad and can be composed of at least about 40% guanosine nucleotides, the nucleotide sequence containing at least two runs of at least two guanosines. Some of the new oligonucleotides also contain phosphorothioate backbones and 3' end modifications. Representative guanosine-rich oligonucleotides of the present invention demonstrate anti-viral activity in tissue culture against HSV-2, HIV-1, HCMV and FMLV, and show specific inhibition of bacterial RNA polymerase enzymes T7 and T3, the FMLV and HIV-1 reverse transcriptase enzyme and eukaryotic RNA polymerase.

22 Claims, 18 Drawing Sheets

OTHER PUBLICATIONS

Gura, "Antisense Has Growing Pains—Efforts to Develop Antisense Compounds for Cancer, AIDS, and Other Diseases Have Encountered Some Unexpected Questions About How the Drugs Really Work," Science, 270, 575–577 (1995).*

Kreig et al., "CpG Motifs in Bacterial DNA Trigger Direct B–Cell Activation," Nature, 374, 546–549 (Apr. 6, 1995).*

Patrick et al., "Antiviral and Resistance Studies of AG1343, an Orally Bioavailable Inhibitor of Human Immunodeficiency Virus Protease," Antimicrobial Agents and Chemotherapy, 40(2), 292–297 (Feb., 1996); supplied but not cited by applicant.*

Rusconi et al., "Naphthalene Sulfonate Polymers with CD4–Blocking and Anti–Human Immunodefiency Virus Type 1 Activities," Antimicrobial Agents and Chemotherapy, 40(1), 234–236 (Jan. 1996); supplied but not cited by applicant.*

Wallace et al.(I), "Pharmacokinetics and Distribution of a $^{33}$P–Labeled Anti–Human Immunodeficiency Virus Oligonucleotide (AR177) After Single– and Multiple–Dose Intravenous Administration to Rats," J. Pharmacology and Experimental Therapeutics, 280(3), 1480–1488 (1997); supplied but not cited by applicant.*

Wallace et al. (II), "Single–Dose Hemodynamic Toxicity and Pharmacokinetics of a Partial Phosphorothioate Anti-–HIV Oligonucleotide (AR177) After Intravenous Administration to Cynomolgus Monkeys," J. Pharmacology and Experimental Therapeutics, 278(3), 1306–1312 (1996); supplied but not cited by applicant.*

Wallace et al. (III), "Repeat–Dose Toxicity and Pharmacokinetics of a Partial Phosphorothioate Anti–HIV Oligonucleotide (AR177) After Bolus Intravenous Administration to Cynomolgus Monkeys," J. Pharmacology and Experimental Therapeutics, 278(3), 1313–1317 (1987); supplied but not cited by applicant.*

Rando, "Clinical Trial Results of Aronex's Anti–HIV Oligonucleotide (AR177) and Recent Antisense Technology Advances," IBC's Fourth International Symposium on Antisense Therapeutics with New Applications for Genomics, International Business Communications, Inc., Wyndham Emerald Plaza Hotel, San Diego, CA, Feb. 6–7, 1997; only abstract supplied; supplied but not cited by applicant.*

Clinical Update, Hybridon, Inc., Worcester, MA, Feb. 10, 1997; press release apparently obtained from the Internet; supplied but not cited by applicant.*

Hybridon Moves GEM® 91 into Confirmatory Clinical Trial in Advanced HIV–Positive Patient, Hybridon, Inc., Cambridge, MA, Feb. 10, 1997; original release date was Feb. 6–7, 1997 in San Diego, CA (See ref. RB supra); supplied but not cited by applicant.*

Kahn et al., "Phase 1 Study of AR–177 (Zintevir), an HIV–1 Inhibitor with Significant Activity Against Integrase Protein: Safety, Pharmacokinetics, Immunologic and Virologic Activity," Abstract of presentation at the 11th International Conference on AIDS, Vancouver, BC, Jul. 7–12, 1996; supplied but not cited by applicant.*

Kern, "Preclinical Evaluation of Antiviral Agents: In Vitro and Animal Model Testing," Ch. 3 in Antiviral Agents and Viral Diseases in Man, Galasso et al. (eds.), Raven Press, Ltd., New York, NY, 1990, pp. 87–114, only pp. 87 and 94–95 supplied.*

Balzarini, J., "Suppression of the Breakthrough of Human Immunodeficiency Virus Type 1 (HIV–1) in Cell Culture by Thiocarboxanilide Derivatives When Used Individually or in Combination with Other HIV–1–Specific Inhibitors (i.e., TSAO Derivatives)," Proc. Natl. Acad. Sci. USA 92:5470–5474 (Jun. 1995).

Nagy, K. et al., "Antiviral Activity of Human Immunodeficiency Virus Type 1 Protease Inhibitors in a Single Cycle of Infection: Evidence for a Role of Protease in the Early Phase," J. Virol. 68:757–765 (Feb. 1994).

Nelson el al., "Bifunctional Oligonucleotide Probes Synthesized Using a Novel CPG Support Are Able to Detect Single Base Pair Mutations," Nucleic Acids Research, 17:7187–7194 (1989). (issue No. 18).

Nelson et al., "A New and Versatile Reagent for Incorporating Multiple Primary Aliphatic Amines into Synthetic Oligonucleotides," Nucleic Acids Research, 17: 7179–7186 (1989). (issue No. 18).

Vlassov et al, "The Effect of Modification of Terminal Groups of Oligonucleotides on Their Stability in Mycoplasma Culture," Biopolim. Kletka, vol. 7, No. 5, (Novosibirsk, USSR), pp. 37–41, see Biosis, Abstract No. 94–032, 483, (1994).

Zendegui et al, "In Vivo Stability and Kinetics of Absorption and Disposition of 3'Phosphopropyl Amine Oligonucleotides," Nucleic Acids Research, 20: 307–314 (1992). (issue No. 2).

Agrawal S. et al., "Oligodeoxynucleoside Phosphoramidates and Phosphorothioates as Inhibitors of Human Immunodeficiency Virus" Proceedings of the National Academy of Sciences of USA, vol. 85, Oct. 1, 1998, pp. 7079–7083.

Wyatt, J. et al., "Combinatorially selected guanosine–quartet structure is a potent inhibitor of human immunodeficiency virus envelope–mediated cell fusion" Proceedings of the National Academy of Sciences of USA., vol. 91, Feb. 1994.

Rando, R. et al., "Suppression of human immunodeficiency virus type 1 activity in vitro by oligonucleotides which form intramolecular tetrads" Journal of Biological Chemistry., vol. 270, Jan. 27, 1995, pp. 1754–1760.

Supplementary Partial European Search Report, dated Jul. 16, 1998, that was received in EPC counterpart application EP 94 917899, filed on Apr. 25, 1994.

* cited by examiner

ANTI-VIRAL GUANOSINE-RICH OLIGONUCLEOTIDES

This application is a continuation-in-part of U.S. Pat. App. No. 08/145,704 filed Oct. 28, 1993 (now U.S. Pat. No. 5,567,604), which is a continuation-in-part of U.S. Pat. App. No. 08/053,027 filed Apr. 23, 1993 (abandoned). This application is also a U.S. national phase application of Patent Cooperation Treaty App. No. PCT/US94/04529 filed Apr. 25, 1994, which is a continuation-in-part of U.S. Pat. App. No. 08/145,704 filed Oct. 28, 1993 (now U.S. Pat. No. 5,567,604) and a continuation-in-part of U.S. Pat. App. No. 08/053,027 filed Apr. 23, 1993 (abandoned).

BACKGROUND OF THE INVENTION

1. Field of the Invention

The present invention relates generally to the field of oligonucleotide chemistry and anti-viral pharmacotherapy. More specifically, the present invention relates to novel guanosine-rich oligonucleotides and their use as novel anti-viral agents.

2. Description of the Related Art

Previously, it was believed that "antisense" oligonucleotides inhibit viruses by interfering with protein translation via an RNA:DNA duplex structure. More recent research, however, indicates a variety of possible mechanisms by which oligonucleotides inhibit viral infections. For example, oligodeoxycytidine (poly SdC) inhibits HIV-1. Marshall et al., PNAS (1992) 89:6265–6269, discussed the potential mechanism (competitive inhibition) by which oligodeoxycytidine directly inhibits viral reverse transcriptase. Poly SdC also inhibited AMV reverse transcriptase and Pol I (Klenow fragment) and polymerase $\alpha$, $\beta$ and $\gamma$. Previously, Matsukura et al., PNAS (1987) 84:7706–7710, used a similar phosphorothioate derivative of oligodeoxycytidine to demonstrate inhibition of HIV-1 in culture. Marshall and Caruthers, Science (1993) 259:1564–1569, reported the use of diphosphorothioate oligonucleotides, e.g., antisense specific, random nucleotide combinations and oligodeoxycytidine against HIV-1. In all cases, the mechanism of action was attributed to a direct inhibition of HIV-1 reverse transcriptase. Other potential mechanisms of anti-viral action of oligonucleotides were postulated by Boiziau et al., PNAS (1992) 89:768–772, e.g., promotion of RNAse H activity and inhibition of reverse transcriptase initiating cDNA synthesis. In addition, Goa et al., Molecular Pharmacology (1992) 41:223–229 reported that phosphorothioate oligonucleotides inhibit human DNA polymerases and RNAse H, and the adsorption or penetration of the virus into cells. Iyer et al., Nucleic Acids Research (1990) 18:2855–2859 report that if a base was removed from an anti-sense polynucleotide forming an abasic site, the compound did not lose its activity which argues against the need for the formation of an RNA:DNA antisense mediated hybrid for anti-viral activity. Stein et al. have characterized the interaction of poly SdC with the V3 loop of HIV-1 gp120, and postulated that the specific interaction of poly SdC with the HIV-1 V3 loop may be a mechanism by which an oligonucleotide could inhibit HIV-1 in vivo.

It is known that synthetic oligonucleotides may be designed which are capable of binding to duplex DNA to form triplex DNA. See U.S. Pat. No. 5,176,996 Hogan & Kessler issued Jan. 5, 1993. This application describes a method for making synthetic guanosine-rich oligonucleotides which are targeted to specific sequences in duplex DNA and which form colinear triplexes by binding to the major groove of the DNA duplex.

SUMMARY OF THE INVENTION

In one embodiment of the present invention, there is provided a method of treating a pathophysiological state caused by a virus, comprising the step of administering a pharmacological dose of an oligonucleotide, said dose being sufficient to inhibit production of said virus, wherein said oligonucleotide contains a high percentage of guanosine bases. In a particular embodiment, the oligonucleotide has a three dimensional structure and this structure is stabilized by guanosine tetrads. In a further embodiment, the oligonucleotide has two or more runs of two contiguous deoxyguanosines.

In another embodiment of the present invention, there is provided a method of treating a pathophysiological state caused by a herpes simplex virus, comprising the step of administering a pharmacological dose of an oligonucleotide, said dose being sufficient to inhibit the replication of said virus, wherein said oligonucleotide contains a high percentage of guanosine bases. In a particular embodiment, the oligonucleotide has a three dimensional structure and this structure is stabilized by guanosine tetrads.

In a further embodiment, the oligonucleotide has two or more runs of two contiguous deoxyguanosines.

In yet another embodiment of the present invention, there is provided a method of treating a pathophysiological state caused by human immunodeficiency viruses, comprising the step of administering a pharmacological dose of an oligonucleotide, said dose being sufficient to inhibit the replication of said virus, wherein said oligonucleotide contains a high percentage of guanosine bases. In a particular embodiment, the oligonucleotide has a three dimensional structure and this structure is stabilized by guanosine tetrads. In a further embodiment, the oligonucleotide has two or more runs of two contiguous deoxyguanosines.

In still yet another embodiment of the present invention, there is provided a method of treating a pathophysiological state caused by human papilloma virus, comprising the step of administering a pharmacological dose of an oligonucleotide, said dose being sufficient to inhibit the replication of said virus, wherein said oligonucleotide contains a high percentage of guanosine bases. In a particular embodiment, the oligonucleotide has a three dimensional structure and this structure is stabilized by guanosine tetrads. In a further embodiment, the oligonucleotide has two or more runs of two contiguous deoxyguanosines.

In still yet another embodiment of the present invention, there is provided a method of treating a pathophysiological state caused by human cytomegalovirus, comprising the step of administering a pharmacological dose of an oligonucleotide, said dose being sufficient to inhibit the replication of said virus, wherein said oligonucleotide contains a high percentage of guanosine bases. In a particular embodiment, the oligonucleotide has a three dimensional structure and this structure is stabilized by guanosine tetrads. In a further embodiment, the oligonucleotide has two or more runs of two contiguous deoxyguanosines.

In still yet another embodiment of the present invention, there is provided a method of treating a pathophysiological state caused by adenovirus, comprising the step of administering a pharmacological dose of a oligonucleotide, said dose being sufficient to inhibit the replication of said virus, wherein said oligonucleotide contains a high percentage of guanosine bases. In a particular embodiment, the oligonucleotide has a three dimensional structure and this structure is stabilized by guanosine tetrads. In a further embodiment, the oligonucleotide has two or more runs of two contiguous deoxyguanosines.

In still yet another embodiment of the present invention, there is provided a method of treating a pathophysiological state caused by hepatitis B virus, comprising the step of administering a pharmacological dose of a oligonucleotide, said dose being sufficient to inhibit the replication of said virus, wherein said oligonucleotide contains a high percentage of guanosine bases. In a particular embodiment, the oligonucleotide has a three dimensional structure and this structure is stabilized by guanosine tetrads. In a further embodiment, the oligonucleotide has two or more runs of two contiguous deoxyguanosines.

In still yet another embodiment of the present invention, there is provided a guanosine-rich oligonucleotide having a three dimensional structure, wherein the three dimensional structure is stabilized by guanosine tetrads or at least two runs of two contiguous deoxyguanosines and wherein these oligonucleotides exhibit anti-viral activity.

In a further embodiment, the oligonucleotides of the present invention have partially or fully phosphorothioated internucleoside linkages (backbones) or other chemical modifications.

In a further embodiment, the oligonucleotides of the present invention have chemically modified or unnatural (synthetic) bases.

BRIEF DESCRIPTION OF THE DRAWINGS

FIG. 5A shows that the reduction in full length transcripts directed by the T7 and T3 promoter when I100-51 (antiparallel triple helix forming oligonucleotide; FMLV2ap) was added. Samples in which no oligonucleotide was added were counted and used as 100% transcription reference points. In all other reactions 4×10$^{-6}$M of G101-50 (4e-6) was added and where indicated G101-50 plus I100-51 at concentrations ranging from 2×10$^{-9}$ to 2×10$^{-6}$ M (2e-9 to 2e-6).

FIG. 5B shows the reduction in full length transcript by I100-01 (FMLV2p). T7 directed transcripts were treated as in FIG. A. G101-50 was added to each reaction except the control (no oligo) with or without various concentration of I100-01 or I100-11 (26% G-ctl).

FIG. 5C shows the analysis of truncated (63 base pair) transcript.

FIG. 5B HIV-1 negative PBMCs from two different donors were infected with HIV-1$_{DV}$ and then incubated in the presence of drug for 10 days at which time the culture medium was assayed for the presence of p24 antigen.

DETAILED DESCRIPTION OF THE INVENTION

Figure 1:
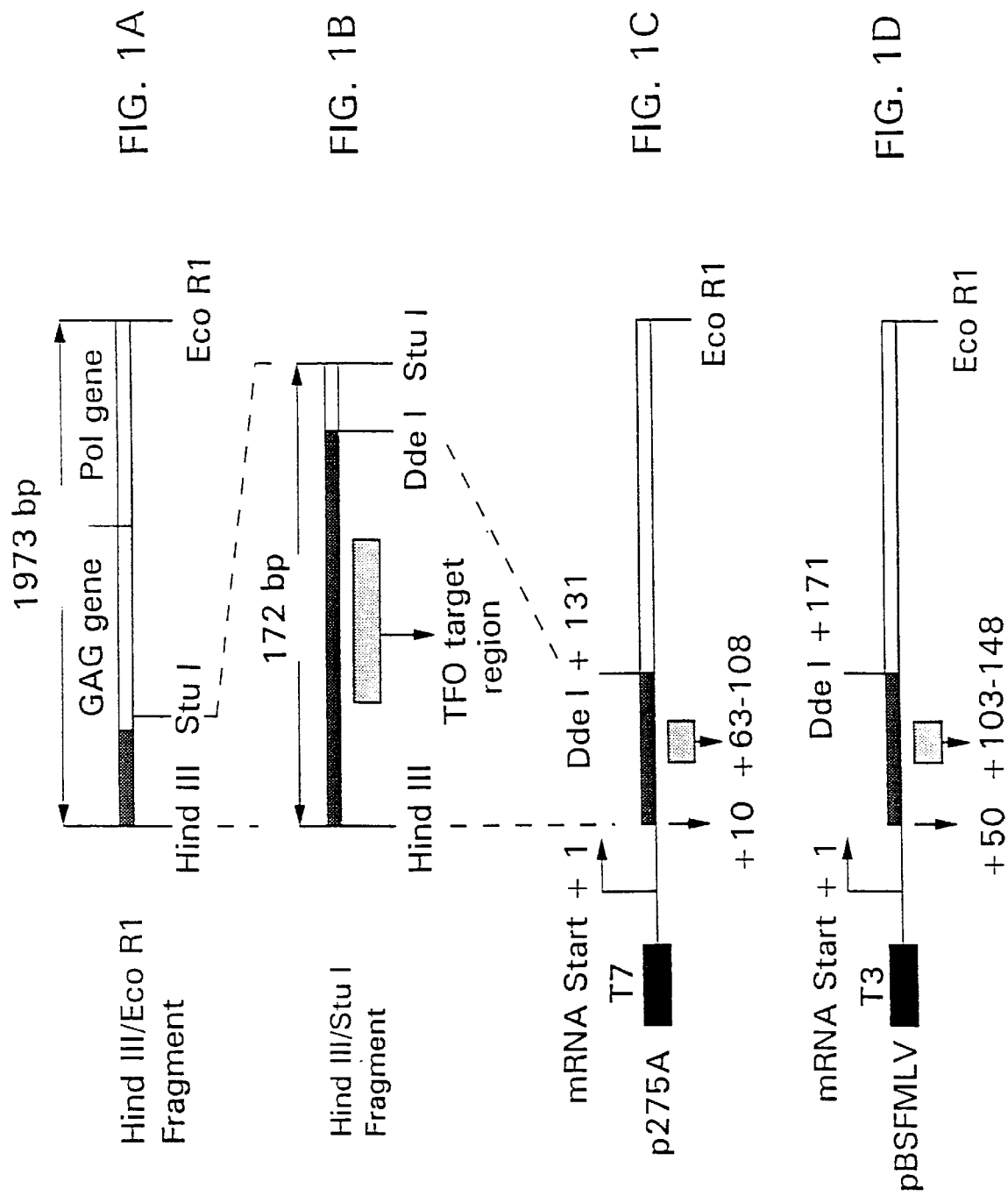
FIG. 1A shows a 1973 base pair Hind III to Eco R1 sub fragment of the Friend Murine Leukemia Virus (FMLV) clone 57 genome.
FIG. 1B shows a 172 base pair (Hind III to Stu I) fragment which is an expanded portion of the 1973 base pair fragment. Within this fragment is the purine rich target to which triple helix forming oligonucleotides are directed.
FIG. 1C shows the entire Hind III/Eco R1 FMLV fragment cloned into the pT7-2 plasmid (United States Biochemical Corporation) yielding p275A. In this recombinant the Hind III site is 10 base pairs downstream of the T7 mRNA start site. The 5' portion of the triple helix target region is 63 base pairs downstream of the mRNA start and the Dde I site is 131 base pairs downstream of the mRNA start site.
FIG. 1D shows the Hind III/Eco R1 FMLV fragment was cloned into pBS (Stratagene) yielding pBSFMLV. The Hind III site, triple helix target site and Dde I site are respectively 50, 103 and 171 base pairs downstream from the mRNA start site.

It is readily apparent to one skilled in the art that various substitutions and modifications may be made to the invention disclosed herein without departing from the scope and spirit of the invention.

The term "oligonucleotide" as used herein is defined as a molecule comprised of two or more deoxyribonucleotides or ribonucleotides, preferably more than ten. Its exact size will depend on many factors including the specificity and antiviral activity of the oligonucleotide for various viruses. In addition, bases can refer to unnatural (synthetic) bases used in place of an A, C, T or G.

In referring to "bases" herein, the term includes both the deoxyribonucleic acids and ribonucleic acids. The following abbreviations are used. "A" refers to adenine as well as to its deoxyribose derivative, "T" refers to thymine, "U" refers to uridine, "G" refers to guanine as well as its deoxyribose derivative, "C" refers to cytosine as well as its deoxyribose derivative. A person having ordinary skill would readily recognize that these bases may be modified or derivatized to optimize the methods of the present invention. In addition, bases can refer to unnatural (synthetic) bases used in place of an A, C, T, or G.

The term "inhibition" of viral replication is meant to include partial and total inhibition of viral replication as well as decreases in the rate of viral replication. The inhibitory dose or "therapeutic dose" of the compounds in the present invention may be determined by assessing the effects of the oligonucleotide on viral replication in tissue culture or viral growth in an animal. The amount of oligonucleotide administered in a therapeutic dose is dependent upon the age, weight, kind of concurrent treatment and nature of the viral condition being treated.

The term "pharmacological dose" as used herein refers to the dose of an oligonucleotide which causes a pharmacological effect when given to an animal or human. The pharmacological dose introduced into the animal or human to be treated, will provide a sufficient quantity of oligonucleotide to provide a specific effect, e.g., (1) inhibition of viral protein or enzymes, (2) inhibition of viral-specific replication, (3) preventing the target site from functioning or (4) damaging the duplex DNA at the specific site or (5) ablating the DNA at the site or (6) inhibiting the transcription/translation of the gene under the regulation of the site being bound or (7) internal inhibition of transcription or translation of the gene containing the sequence. One skilled in the art will readily recognize that the dose will be dependent upon a variety of parameters, including the age, sex, height and weight of the human or animal to be treated, the organism or gene location which is to be attacked and the location of the target sequence within the organism. Given any set of parameters, one skilled in the art will be able to readily determine the appropriate dose.

The term "pathophysiological state" as used herein refers to any abnormal, undesirable or life-threatening condition caused directly or indirectly by a virus.

The term "GTOs" means an oligonucleotide in which there is a high percentage of deoxyguanosine, or contains two or more segments (runs) of two or more deoxyguanosine residues per segment.

As used herein, the term "guanosine tetrads" refers to the structure that is formed of eight hydrogen bonds by coordination of the four O$^6$ atoms of guanine with alkali cations believed to bind to the center of a quadruplex, and by strong stacking interactions. Of particular interest to the I100-15 class of GTO is the structure of the telomere sequence repeat T$_4$G$_4$, first detected in Oxytricha. The oxytricha repeat has been studied in oligonucleotides by NMR and by crystallographic methods. See Smith et al., Nature 1992, 356:164–68, and Kang et al., Nature 1992 356:126–31. As predicted from numerous previous physical and biochemical studies, both the NMR and crystallographic studies suggest that folding is mediated by square planar Hoogsteen H-bonding among G-residues, with overall antiparallel orientation of the four strand equivalents comprising the tetrad fold. As expected, the crystallography has shown that the structure is selectively stabilized by tight binding of a small monovalent cation to the O$^6$ oxygen of guanosine.

The present invention provides a method of treating a pathophysiological state caused by a virus, comprising the step of administering a pharmacological dose of an oligonucleotide, said dose being sufficient to inhibit the replication of said virus, wherein said oligonucleotide contains sufficient contiguous guanosine so that a guanosine tetrad (inter- or intra-molecular) can form, and the three dimensional structure of the oligonucleotide is stabilized by guanosine tetrads formed at strategic locations. Generally, this method of treating a virus-induced pathophysiological state may be useful against any virus. More preferably, the methods of the present invention may be useful in treating pathophysiological states caused by viruses such as herpes simplex virus, human papilloma virus, Epstein Barr virus, human immunodeficiency virus, adenovirus, respiratory syncytial virus, hepatitis B virus, human cytomegalovirus and HTLV I and II.

Generally, the oligonucleotides of the present invention contain a percentage of guanosine bases high enough to ensure anti-viral efficacy. The guanosine is important in forming tetrads which stabilize the three dimensional structure of the Oligonucleotides. Thus, the oligonucleotides of the present invention may have any percentage of guanosine bases which will allow for tetrad formation provided that the oligonucleotide exhibits anti-viral activity. Preferably, the oligonucleotides of the present invention contain two or more segments of two or more guanosine bases, and an overall high percentage of G.

Generally, the oligonucleotides of the present invention may be capped at either the 3' or the 5' terminus with a modifier. Preferably, the modifier is selected from the group consisting of polyamine or similar compounds that confer a net positive charge to the end of the molecule, poly-L-lysine or other similar compounds that enhance uptake of the oligonucleotide, cholesterol or similar lipophilic compounds that enhance uptake of the oligonucleotide and propanolamine or similar amine groups that enhance stability of the molecule.

The phosphodiester linkage of the oligonucleotides of the present invention may be modified to improve the stability or increase the anti-viral activity. For example, the phosphodiester backbone of the oligonucleotide may be modified to a phosphorothioate linkage. Other such modifications to the oligonucleotide backbone will be obvious to those having ordinary skill in this art.

The present invention also provides specific methods of treating viral states. For example, the present invention provides a method of treating a pathophysiological state caused by a herpes simplex virus, comprising the step of administering a pharmacological dose of an oligonucleotide, said dose being sufficient to inhibit the replication of said virus, wherein the three dimensional structure of said oligonucleotide is stabilized by the formation of guanosine tetrads. Also provided in the instant application is a method of treating a pathophysiological state caused by human immunodeficiency virus, comprising the step of administering a pharmacological dose of an oligonucleotide, said dose being sufficient to inhibit the replication of said virus, wherein the three dimensional structure of said oligonucleotide is stabilized by the formation of guanosine tetrads. The present invention also provides a method of treating a pathophysiological state caused by human papilloma virus, comprising the step of administering a pharmacological dose of an oligonucleotide, said dose being sufficient to inhibit the replication of said virus, wherein the three dimensional structure of said oligonucleotide is stabilized by the formation of guanosine tetrads. In addition, the present invention provides a method of treating a pathophysiological state caused by human cytomegalovirus, comprising the step of administering a pharmacological dose of an oligonucleotide, said dose being sufficient to inhibit the replication of said virus, wherein the three dimensional structure of said oligonucleotide is stabilized by the formation of guanosine tetrads. The present invention also provides a method of treating a pathophysiological state caused by hepatitis B virus, comprising the step of administering a pharmacological dose of an oligonucleotide, said dose being sufficient to inhibit the replication of said virus, wherein the three dimensional structure of said oligonucleotide is stabilized by the formation of guanosine tetrads.

This invention discloses a novel anti-viral technology. The total number of antiviral mechanisms by which oligonucleotides, and especially G-rich oligonucleotides, work is not completely known. However in the different virus culture systems listed above, G-rich oligonucleotides were able to significantly reduce virus production in each, and the present invention is drawn to oligonucleotides that have three dimensional structures stabilized by the formation of guanosine tetrads. Prior to this invention, investigators tried to establish anti-viral mechanism based on antisense technology, and yet the present invention shows that oligonucleotide exhibition of anti-viral activity may not be via inhibition of translation events.

The present invention demonstrates poly and/or oligonucleotides inhibit growth of HIV-1, HSV1, HSV2, FMLV and HCMV and other viruses if the molecule contains a high percentage of ribo- or deoxyriboguanosine. The rest of the molecule is composed of thymine, cytosine, xanthosine or adenine nucleotides (ribo- or deoxyribo-), their derivatives, or other natural or synthetic bases. The 5' and 3' termini of the oligonucleotide can have any attachment which may enhance stability, uptake into cells (and cell nuclei) or anti-viral activity. The backbone which connects the nucleotides can be the standard phosphodiester linkage or any modification of this linkage which may improve stability of the molecule or anti-viral activity of the molecule (such as a phosphorothioate linkage).

Structural formulas for several different G-rich oligonucleotides disclosed in the instant invention are listed below in Table 1. All oligonucleotides listed here have a propanolamine group attached to their 3' end. This amine group confers stability against nuclease digestion to these oligonucleotides.

TABLE 1

| | |
|---|---|
| SEQ ID NO 5(B106-62) | 5'-gtggtggtggtgttggtggtggtttggggggtgggg-3' |
| SEQ ID NO 6(B106-71) | 5'-gtggttggtggtggtgtgtgggtttggggtggggg-3' |
| SEQ ID NO 21(I100-01) | 5'-tggtgggtgtgtggggggtgttgggggttgttggtggggtggtgg-3' |
| SEQ ID NO 24(I100-07) | 5'-gtggtgggtgggtgggtggtgggtggtggttgtgggtgggtggtg-3' |

TABLE 1-continued

| SEQ ID NO 28 (I100-50) | 5'-ggtggtggggtggttgttggggttg-3' |
| --- | --- |
| SEQ ID NO 29 (I100-51) | 5'-ggtggtggggtggttgttggggttgttgggggtgtgtgggtggt-3' |
| SEQ ID NO 26 (I100-11) | 5'-gatccatgtcagtgacactgcgtagatccgatgatccagtcgatg-3' |
| SEQ ID NO 12 (G101-50) | 5'-ggtgggtggtttgtgtggttggtgggttttt-3' |
| SEQ ID NO 13 (G105-50) | 5'-gggggggggggtgtgggggggggttgtggtgg-3' |
| SEQ ID NO 14 (G106-50) | 5'-ggtgggtgggttgggggtgggtgggg-3' |
| SEQ ID NO 15 (G109-50) | 5'-tggggtttgggtgggggttgggtggttg-3' |
| SEQ ID NO 16 (G110-50) | 5'-gggtggtggtgttggtgttgtgtg-3' |
| SEQ ID NO 17 (G113-50) | 5'-ggtgggggggttggtgtgtttg-3' |
| SEQ ID NO 1 (A100-00) | 5'-tgggtgggtgggtgggggggtgtgggtgtggggtg'3' |
| SEQ ID NO 2 (A100-50) | 3'-tgggtgggtgggtgggggggtgtgggtgtggggtg-5' |
| SEQ ID NO 4 (A101-00) | 5'-ggtggtgggggggtgggtggtggtgggggtgttgg-3' |
| SEQ ID NO 18 (HIV26ap) | 5'-gtgtggggggtgggtgggtgggt-3' |
| SEQ ID NO 19 (HIV26ctl) | 5'-gggtgggtgggtgggtgggtgggtgg-3' |
| SEQ ID NO 9 (B107-51) | 5'-ggtgggtggtggtggttggggggggggggt-3' |
| SEQ ID NO 10 (B133-55) | 5'-ggtggttgggggtggggggg-3' |
| SEQ ID NO 11 (B133-55) | 5'-gggtggggtggtgggtggggg-3' |
| SEQ ID NO 20 (I100-00) | 5'-gttgggggttgttggtggggtggtgg-3' |
| SEQ ID NO 27 (I100-12, PT) | 5'-gttgggggttgttggtggggtggtgg-3' |
| SEQ ID NO 22 (I100-05) | 5'-tggtgggtgtgtgggggggtgttggggggttgttggtggggtggtgg-CHOL |
| SEQ ID NO 23 (I100-06) | 5'-gtggtgggtgggtgggtggtgggtggtggttgtgggtgggtggtg-CHOL |
| SEQ ID NO 25 (I100-08) | 5'-gttgggggttgttggtggggtggtgg-CHOL |
| SEQ ID NO 3 | 5'-gggtgggtgggtgggtgg-3' |
| SEQ ID NO 30 | 5'-gggtggttgggtggttgg-3' |
| SEQ ID NO 31 (1173) | 5'-gggtgggtgggtgggtgg-3' |
| SEQ ID NO 32 (1174, PT) | 5'-gggtgggtgggtgggtgg-3' |
| SEQ ID NO 33 (I100-15) | 5'-gtggtgggtgggtgggt-3' |
| SEQ ID NO 34 (I100-16) | 5'-gtggtgggtgggtgggtggtgggtggt-3' |
| SEQ ID NO 35 (I100-17) | 5'-gtggtgggtgggtgggtggtgggtggtggttgtgggt-3' |
| SEQ ID NO 36 (I100-18) | 5'-ttgtgggtgggtggtg-3' |
| SEQ ID NO 37 (I100-19) | 5'-tggtgggtggtggttgtgggtgggtggtg-3' |
| SEQ ID NO 38 (I100-20) | 5'-gtgggtgggtggtgggtggtggttgtgggtgggtggtg-3' |
| SEQ ID NO 39 (I100-21, PT) | 5'-gtggtgggtgggtgggtggtgggtggtggttgtgggtgggtggtg-3' |
| SEQ ID NO 40 (1231) | 5'-gatccatgtcagtgacac-3' |
| SEQ ID NO 41 (1232, PT) | 5'-gatccatgtcagtgacac-3' |
| SEQ ID NO 42 (1229) | 5'-cccccccccccccccccc-3' |
| SEQ ID NO 43 (1230, PT) | 5'-cccccccccccccccccc-3' |
| SEQ ID NO 44 (1198) | 5'-ttcatttgggaaacccttggaacctgactgactggccgtcgttttac-3' |

TABLE 1-continued

| | |
|---|---|
| SEQ ID NO 45(1200) | 5'-gtaaaacgacggcca-3' |
| SEQ ID NO 46(I100-25) | 5'-gtggtgggtgggtgggg-3' |
| SEQ ID NO 47(I100-26) | 5'-gtggtgggtgggtggg-3' |
| SEQ ID NO 48(I100-35) | 5'-tggtgggtgggtgggt-3' |
| SEQ ID NO 49(I100-27) | 5'-gtggtgggtgggt-3' |
| SEQ ID NO 50(I100-28) | 5'-gtggtgggt-3' |
| SEQ ID NO 51(I100-30) | 5'-gtgggtgggtgggt-3' |
| SEQ ID NO 52(I100-29) | 5'-gtgggtgggt-3' |

The present invention also provides novel guanosine-rich oligonucleotides having anti-viral activity.

The following examples are offered by way of illustration and are not intended to limit the invention in any manner.

EXAMPLE 1

HSV-2 CULTURE ASSAY

In viral yield reduction assays, Vero cells ($4 \times 10^4$ cells/tissue culture well) were incubated with oligonucleotide(s) for 14 hours before the oligonucleotide was removed and virus (HSV-2 strain HG52) added to the cells at a multiplicity of infection (m.o.i.) of 0.1 to 1.0 ($4 \times 10^3$ to $4 \times 10^4$ PFU). The infection was allowed to proceed for 10 minutes after which the cells are washed and fresh media, containing the same oligonucleotide is added for an additional 14 hours. Then the cells are subjected to a freeze/thaw lysis after which the released virus is titered.

EXAMPLE 2

HIV-1 CULTURE ASSAY

The SUP T1 T lymphoma cell line was infected with HIV-1 strain DV at a multiplicity of infection (m.o.i.) of 0.1 for one hour at 37° C. After the infection, free virus was washed off and the newly infected cells were plated ($5 \times 10^4$ cells) in quadruplicate in 96 well plates that had been prepared with various dilutions of oligonucleotide. The final concentration of drug varied between 0.1 and 20 uM. After 3 days of incubation at 37° C., the plates were scored for the presence of multinucleated giant cells (syncytia).

In assays designed to inhibit syncytia formation, a number of oligonucleotides exhibited anti-HIV-1 activity. The oligonucleotides and their ED50 are listed in Table 2. I100-05 is the same as I100-01 with a cholesterol group attached to the 3' end via a triglycyl-linker. I100-08 is the same as I100-00 with a cholesterol group attached to the 3' end via a triglycyl-linker. I100-07 was designed as a sequence isomer to I100-01 and I100-06 is the cholesterol derivative of I100-07. A100-00 is the same sequence in the opposite orientation to HIB38p (A100-50). I100-07, originally designed as a control for I100-01 to be used in anti-FMLV experiments, was the most efficacious oligonucleotide tested against HIV-1.

Figure 3:
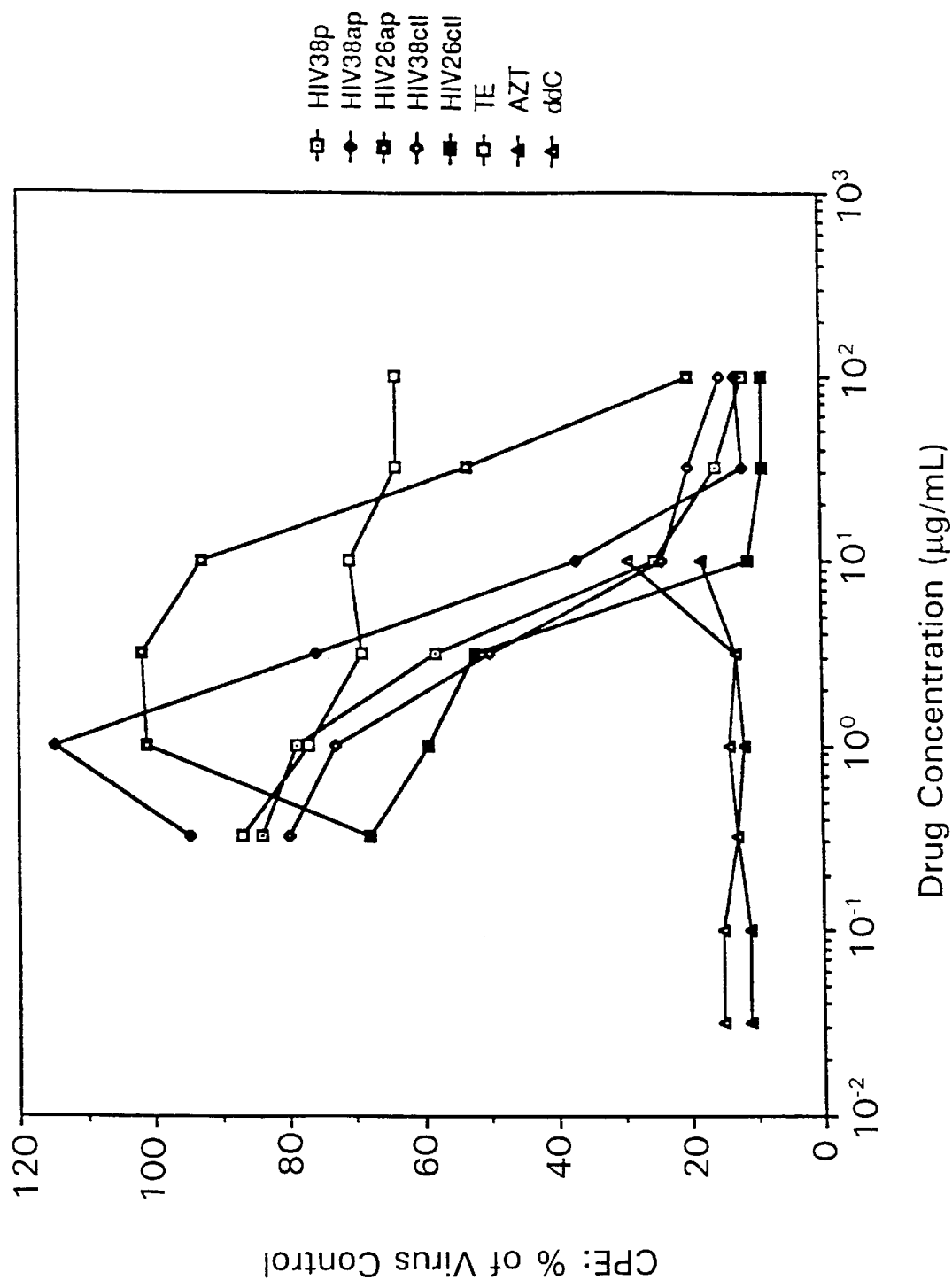
FIG. 3 shows that the MT-2 cells infected with 0.01 m.o.i. of HIV-1 were treated with various concentrations of oligonucleotide or AZT or ddC. The data represents the number of viable cells remaining in the culture dish, i.e., not undergoing virus induced cytopathic effects (CPE). In this graph, 100% is the level of CPE occurring in cultures infected with virus but not treated with any drug.

In other experiments, the HIV-1 strain LAV was used to infect MT-2 cells at an m.o.i of 0.01. After 7 days, these cells were scored for cytopathic effects (CPE). In anti-HIV-1 assays in which MT-2 cells were infected at an m.o.i. of 0.01, several G-Rich oligonucleotides were able to inhibit viral-induced cytopathic effects with effective dose 50's (ED50s) in the 0.5–1.0 uM range (FIG. 3). The oligonucleotides shown in FIG. 3 were effective in the 0.5 to 1.0 uM range, including A100-00 (HIV38p) and A100-50 (HIV38ap), A101-00 (HIV38ctl), HIV-26ctl. The oligonucleotide HIV-26ap exhibited less efficacy in this assay with an ED50 in the 5 to 10 uM range. In FIG. 3, TE represents buffer alone, i.e., no drug, while AZT and ddC are control drugs.

TABLE 2

$ED_{50}$ for oligonucleotides in an anti-HIV-1 syncytia formation assay.

| G-Rich oligonucleotide | ED50 |
|---|---|
| I100-00 | 3.75 µM |
| I100-01 | 4.50 µM |
| I100-05 | 3.25 µM |
| I100-08 | 3.25 µM |
| I100-06 | 0.70 µM |
| I100-07 | 0.25 µM |
| A100-00 | 3.25 µM |

EXAMPLE 3

FMLV CULTURE ASSAY

Friend Murine Leukemia Virus (FMLV) was grown in a chronically infected murine fibroblast cell line (pLRB215) or can be propagated in an acute assay system by infection of NIH3T3 cells. When the chronically infected cell line was used, pLRB215 cells were split ($1 \times 10^5$) into 24 well culture dishes and incubated 16 to 20 hours at 37° C. The media was then removed and replaced with media containing various concentrations of oligonucleotide. After 1, 3 or 5 days, culture media was assayed for the presence of the viral reverse transcriptase enzyme.

In acute assays, NIH3T3 cells were split ($1 \times 10^4$) into 96 well dishes and allowed to incubate for 16–20 hours. After incubation, culture media was removed and concentrated virus stock (10 ul) was added to each well in 100 ul of completed media containing 2 ug/ml polybrene. The virus infection was allowed to proceed for 18 hours at which time the virus containing media was removed and complete media containing various concentrations of oligonucleotide was added. After 4 to 7 days, the culture media was assayed for the presence of viral reverse transcriptase.

EXAMPLE 4

HCMV CULTURE ASSAY

Human cytomegalovirus was cultured in the human diploid lung fibroblast cell line MRC-5. These cells were split and placed into 24 well culture dishes and preincubated for 24 hours with various concentrations of oligonucleotide (0.5 to 20 uM) in complete media. The oligonucleotide was then washed off and virus was added to the cells (approximately 0.1 m.o.i.) for 2 hours at 37° C. The virus was then removed and complete media containing the same concentration of oligonucleotide was added. Cells were then placed at 37° C. for 10–12 days at which time virus in the culture media was titered using a standard agar overlay procedure.

EXAMPLE 5

BACTERIAL T3 AND T7 ASSAYS

In this assay system, a 2 kb fragment (HindIII to Ecor R1) of the FMLV virus (clone 57) was molecularly cloned between the Hind III/Eco R1 sites 10 bp downstream of the bacterial T7 promoter (p275A) or 50 bp downstream of the bacterial T3 promoter (pBSFMLV2). A schematic representation of these two recombinant plasmids can be seen in FIG. 1. Isolated recombinant DNA was then digested with Dde I. Oligonucleotides were incubated then with the digested DNA and then subjected to in-vitro transcription using either the T7 or T3 bacterial enzymes.

EXAMPLE 6

REVERSE TRANSCRIPTASE ASSAY

In this assay, reverse transcriptase (either MMLV which is commercially available or FMLV from pLRB215 culture media) was incubated with various concentrations of oligonucleotide and then assayed using the enzyme linked oligonucleotide sorbent assay (ELOSA), the ELOSA kit is commercially available from New England Nuclear.

EXAMPLE 7

EUKARYOTIC IN VITRO TRANSCRIPTION

In this assay, a recombinant plasmid containing the HSV-1 IE175 promoter fused to the bacterial chloramphenicol acetyltransferase gene (CAT) was linearized and used as a template for run off transcription studies. The commercially available HeLa cell nuclear extracts or prepared nuclear extracts of HSV-2 infected VERO cell were used.

EXAMPLE 8

INHIBITION OF HSV-2 ACTIVITY

Figure 2:
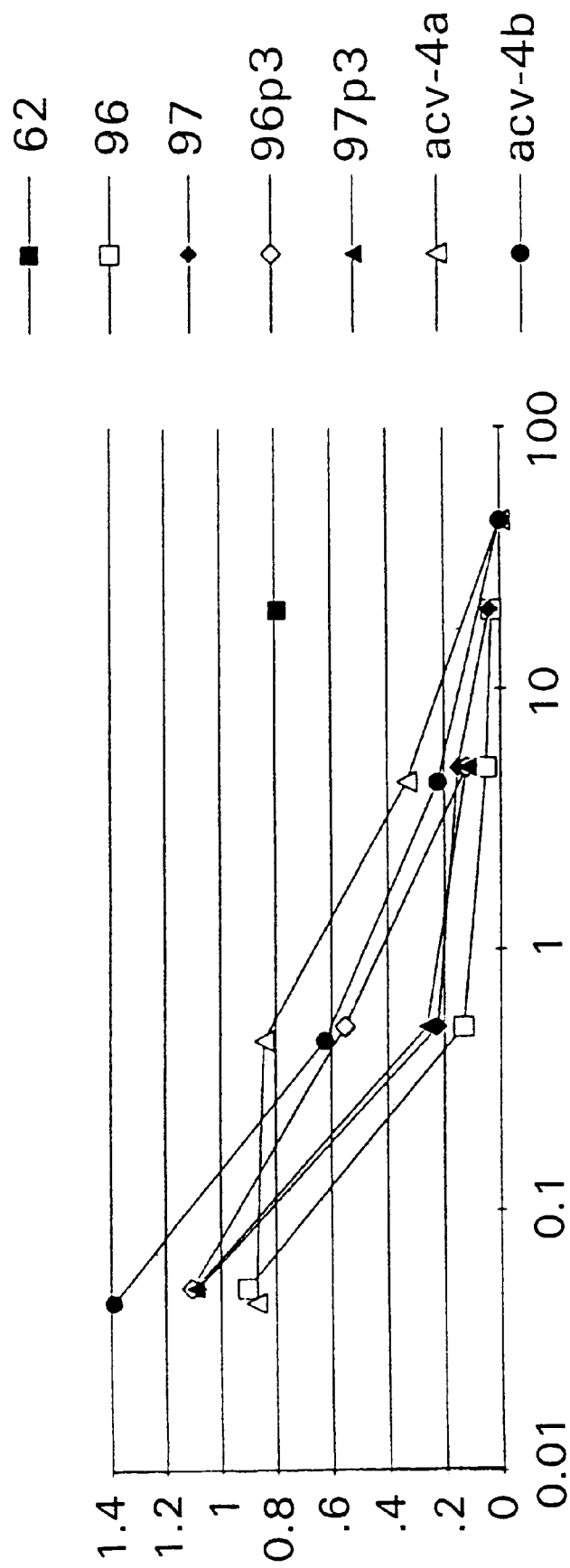
FIG. 2 shows that G-Rich phosphorothioated-oligonucleotides induced reduction in HSV-2 viral titer. VERO cells infected with HSV-2 were treated with various concentrations of the indicated drug. The results are plotted as percent virus yield relative to VERO cells infected with virus but not treated with drug (titer=1). The filled square (B106-62) represents a single concentration point (20 $\mu$M) for this oligonucleotide. B106-96 is the fully phosphorothioated version of B106-62. B106-97 is the fully phosphorothioated version of B106-71. ACV (4a and 4b) is acyclovir tested against two different stock concentrations of HSV-2 strain HG52. In two experiments, after virus infection and before reapplication of oligonucleotide, the cells were rinsed with a pH 3 buffer in order to remove all virus not yet internalized (96p3 and 97p3).

The oligonucleotide B106-62 was originally designed to form a triple helix structure with a portion of the promoter region of the major immediate early protein of HSV-2 (IE175). The phosphorothioate derivatives of these two oligonucleotides were synthesized and tested for anti-viral activity against HSV-2. FIG. 2 shows that the B106-62 oligonucleotide at 20 $\mu$M was able to reduce viral titers by approximately 20% whereas the phosphorothioate version (B106-96) reduced virus by 50% in the submicromolar concentration range. The control oligonucleotide (B106-97), the phosphorothioate backbone derivative of B106-71, was also able to inhibit virus at the same levels as B106-96. Even when an extensive washing procedure at a pH of 3 was employed to remove excess virus not internalized during the infection, incubation with both B106-96 and B106-97 were able to significantly reduce virus yield. Thus, the mechanism of anti-viral activity was not just blocking adsorption of HSV-2 virions to cells.

FIG. 2 also shows the results of acyclovir in the same molar range as the oligonucleotides. Acyclovir was tested against two different stocks of HSV-2 strain HG52, as illustrated in FIGS. 4a and 4b.

EXAMPLE 9

A. OLIGONUCLEOTIDE SYNTHESIS

The 47-mer DNA template oligonucleotide used was SEQ.ID. NO. 44 (1198) and the 15-mer primer sequence was SEQ.ID. NO. 45 (1200). All oligonucleotides used in these examples were synthesized on a DNA synthesizer (Applied Biosystems, Inc., model 380B or 394), using standard phosphoramidite methods. All oligonucleotides were synthesized with an amino modified 3'-terminal, which results in the covalent attachment of a propanolamine group to the 3'-hydroxyl group or with a cholesterol moiety attached to the 3'-terminal via a triglycyl-linker. Oligonucleotides used in this example were capped at their 3'-terminal with either a propanolamine or a cholesterol moiety to reduce degradation by cellular exonucleases. Phosphorothioate containing oligonucleotides were prepared using the sulfurizing agent TETD. The 3'-cholesteryl modified oligonucleotides were prepared and purified as described by Vu et al. (in *Second International Symposium on Nucleic Acids Chemistry*, Sapporo, Japan, 1993).

B. STABILITY AND TOXICITY

Oligonucleotides with either full length phosphodiester (PD) or full length phosphorothioate (PT) backbones were stable in the culture media for 4 days while oligonucleotides consisting of a more random composition of nucleotides were rapidly degraded. This indicates that the 3'-modified G-rich oligonucleotides with PD backbones were stable against both endonuclease and exonuclease digestion over a defined four day incubation in culture. The concentration of oligonucleotide needed to reduce cell proliferation by 50% ($TC_{50}$) of selected compounds, based on the dye metabolism assay was approximately 40 to 50 $\mu$M for oligonucleotides with PD backbones and 15 to 40 $\mu$M for those compounds containing a PT backbone. The $TC_{50}$ for selected oligonucleotides are presented in Table 3.

TABLE 3

Guanosine/thymidibne and control oligonucleotide sequences

| Oligo[a] | Length | 3'-Modification[b] | Sequence | $TC_{50}$[c] |
|---|---|---|---|---|
| I100-07 | 45 mer | amine | 5'-gtggtggtgggtgggtggtgggtggtggttgtgggtgggtggtg-3' | >50 $\mu$M |
| I100-06 | 45 mer | cholestreol | 5'-gtggtgggtgggtgggtggtgggtggtggttgtgggtgggtggtg-3' | |
| I100-00 | 26 mer | amine | 5'-                  gttgggggttgttggtggggtggtgg-3' | 37 $\mu$M |

TABLE 3-continued

Guanosine/thymidibne and control oligonucleotide sequences

| Oligo[a] | Length | 3'-Modification[b] | Sequence | TC$_{50}$[c] |
|---|---|---|---|---|
| I100-08 | 26 mer | cholestrol | 5'-                      gttgggggttgttggtggggtggtgg-3' | |
| I100-12 | 26 mer | amine(PT) | 5'-                      gttgggggttgttggtggggtggtgg-3' | 18 μM |
| I100-01 | 45 mer | amine | 5'-tggtgggtgtgtgggggggtgttgggggttgttggtggggtggtgg-3' | |
| I100-05 | 45 mer | cholestrol | 5'-tggtgggtgtgtgggggggtgttgggggttgttggtggggtggtgg-3' | |
| A100-00 | 38 mer | amine | 5'-tgggtggggtggggtgggggggtgtggggtgtggggtg       -3' | |
| 1173 | 18 mer | amine | 5'-gggtgggtgggtgggtgg                           -3' | |
| I100-11 | 45 mer | amine | 5'- gatccatgtacgtgacactgcgtagtccgatgatcagtcgatg-3' | 46.5 μM |
| 1231 | 18 mer | amine | 5'-gatccatgtcagtgacac                           -3' | |
| 1229 | 18 mer | amine | 5'-cccccccccccccccccc                           -3' | |

[a]All oligonnucleotides listed were synthesized with phosphodiester backbones except I100-12 which had phosphorothioate (PT) linkages.
[b]The capping group at the 3'-end of the oligonucleotide was either a propanolamine or cholestrol moiety.
[c]Median inhibitory (toxic) concentration in tissue culture.

EXAMPLE 10

INHIBITION OF HIV-1 PRODUCTION IN AN ACUTE ASSAY SYSTEM

A. Cytotoxicity and Stability Assays.

The cytotoxicity of selected oligonucleotides was assayed using the CellTiter 96™ Aqueous Non-Radioactivity Cell Proliferation Assay (Promega). This is a colormetric method for determining the number of viable cells in proliferation or chemosensitive assays using a solution if MTS. Dehydrogenase enzymes found in metabolically active cells convert MTS into a formazan product. The SUP T1 cells used in the cytotoxicity assays were in log phase growth at the time of the assay. Cytotoxicity profiles for GTOs with PD backbones such as I100-15 had TC$_{50}$s (50% cytotoxic concentration) in the range of 30 to 50 μM while GTOs with PT backbones such as I100-15 had TC$_{50}$s in the 10 to 30 μM range. The TC$_{50}$ for AZT in this assay format was approximately 10 μM.

Blockage of the hydroxyl terminus of oligonucleotides has been shown by many investigators to greatly reduce degradation by cellular exonucleases therefore all oligonucleotides used in these studies were modified at their 3'-end with either a propanolamine group or a cholesterol group. For stability studies, 10 μM of GTOs were incubated in MEM (GIBCO) supplemented with 10% FBS. Aliquots were taken after 10 min, 1 day, 2 days, 3 days and 4 days. The aliquots at each time point were immediately extracted twice with 50:50 phenol-chloroform solution and then precipitated by the addition of ethanol. The recovered oligonucleotides were 5'-end-labeled using [γ-$^{32}$P]ATP and polynucleotide kinase. The integrity of the oligonucleotides was then analyzed on a 20% polyacrylamide gel with 7 M urea. The results indicate that a portion of each GTO with a PD backbone was present in the culture medium of three to four days while oligonucleotides composed of a more random assortment of all four nucleotides were rapidly degraded. In addition, positions within PD GTOs where there exist two or more contiguous pyrimidines are more susceptible to endonuclease digestion than regions containing purines or alternating purines and pyrimidines.

B. Long term suppression of Acute HIV-1 infections in SUP T1 cells.

The anti-HIV-1 activity of a series of GTOs, with PD backbones, containing different sequences motifs was tested. One of the sequence motifs tested (oligonucleotide I100-07) was 10 fold more active at inhibiting HIV-1 induced syncytium formation than the other motifs tested (e.g. I100-00 shown in Table 1). I100-07 and its derivatives (length and chemical modification) were further tested for their ability to inhibit virus in a dose-dependent fashion by measurement of syncytium formation and viral p24 production. Briefly, HIV-1$_{DV}$ was used to infect the SUP T1 lymphoblastoid cell line at a multiplicity of infection (m.o.i.) of 0.1 TCID$_{50}$ for one hour at 37° C. prior to washing and resuspension in increasing concentrations of GTOs. The cells (2×10$^4$ cells/well) were inoculated in triplicate in 200 ul of RPMI 1640 containing 10% fetal calf serum. Four days later, the number of syncytia per well or the level of p24 in the medium was determined. The results of these assays are presented in Table 4.

TABLE 4

Guanosine/thymidine oligonucleotide sequences.

| Oligo | Length | linkage[a] | Sequence | ED50[b] (uM) Syn | p24 | T.I.[c] |
|---|---|---|---|---|---|---|
| I100 | | | | | | |
| -07 | 45 mer | PD | 5'- gtggtgggtgggtgggtggtgggtggtggttgtgggtgggtggtg | 0.25 | 0.55 | |
| -27 | 45 mer | PT | 5'- gtggtgggtgggtgggtggtgggtggtggttgtgggtgggtggtg | 0.225 | <0.20 | >100 |
| -20 | 38 mer | PD | 5'- gtgggtgggtggtgggtggtggttgtgggtgggtggtg | 1.00 | 1.00 | |
| -19 | 29 mer | PD | 5'- tggtgggtggtggttgtgggtgggtggtg | 3.75 | 2.00 | |
| -18 | 16 mer | PD | 5'- ttgtgggtgggtggtg | 3.75 | 3.00 | |
| -17 | 37 mer | PD | 5'- gtggtgggtgggtgggtggtgggtggtggttgtgggt | 0.30 | 0.20 | |
| -16 | 27 mer | PD | 5'-gtggtgggtgggtgggtggtgggtggt | 0.25 | 0.15 | >200 |
| -15 | 17 mer | PD | 5'-gtggtgggtgggtgggt | 0.125 | 0.08 | >200 |
| -00 | 26 mer | PD | 5'-gttgggggttgttggtggggtggtgg | 3.25 | ND | |
| -12 | 26 mer | PT | 5'-gttgggggttgttggtggggtggtgg | 0.225 | <0.20 | |
| AZT | | | | 0.04 | 0.40 | >200 |

[a]The internucleotide backbone linkages are denoted as PD for phosphodiester and PT for phosphorothioate.
[b]The ED50 values for the syncytium and p24 inhibition assays in uM concentrations.
[c]T.I. = therapeutic index.

The experimental results indicated that GTOs with simple PD linkages were capable of inhibiting HIV-1 syncytia formation and p24 production in culture. To determine the effect of backbone modification on GTO anti-viral activity, the PD backbone in two oligonucleotides sequences motifs was replaced with a PT backbone. The phosphorothioate containing oligonucleotides (I100-12 and I100-21) where then tested for their ability to inhibit HIV-1 induced syncytium formation and production of HIV-1 p24 in the SUP T1 acute assay system (Table 4). The results from these assays indicated that the presence of sulfur molecules in the oligonucleotide backbone greatly enhanced the anti-viral activity of I100-00 (I100-12) but had little if any effect on I100-07 (I100-21) (Table 4).

It was apparent from our studies that the anti-viral activity of I100-07 was maintained when we reduced the length of the molecule to 17 by deleting segments from the 3'-end (I100-15, -16, -17) but not by deletions from the 5'-end (I100-18, -19, -20). To further determine to optimal size of the PD oligonucleotide needed for maximal anti-HIV-1 the I100-15 size variants listed in Table 5 were synthesized and assayed for antiviral activity.

TABLE 5

Inhibition of HIV-1 Induced Syncytia Using Size variants of 1100-15.

| oligo | Sequence | ED50 Syn. (uM) |
|---|---|---|
| I100-15* | 5' gtggtgggtgggtgggt -3' | 0.16 |
| I100-25 | 5' gtggtgggtgggtgggg -3' | 0.25 |
| I100-26* | 5' gtggtgggtgggtggg -3' | 0.12 |
| I100-35 | 5' tggtgggtgggtgggt -3' | 1.75 |

TABLE 5-continued

Inhibition of HIV-1 Induced Syncytia Using Size variants of 1100-15.

| oligo | Sequence | ED50 Syn. (uM) |
|---|---|---|
| I100-27 | 5' gtggtgggtgggt -3' | 4.50 |
| I100-28 | 5' gtggtgggt -3' | 4.50 |
| I100-30 | 5' gtgggtgggtgggt -3' | 4.50 |
| I100-29 | 5' gtgggtgggt -3' | >10.00 |
| AZT | | 0.02 |

*At 5 uM these compounds suppressed virus at least 7 days post-removal of drug. All other compounds at 5 uM wre the same as AZT 7 days after removal of drug.

The duration of the viral suppression was assayed by changing the medium in HIV-1 infected cultures containing 2.5 uM of various oligonucleotides to complete media without added oligonucleotide on day 4 post-viral infection. The production of viral p24 antigen was then assayed on day 7 and day 11 post-infection. The results of this experiment indicated that the shorter variants of I100-07 (I100-15 and I100-16) as well as the PT version of this molecule (I100-21), were capable of totally suppressing HIV-1 p24 production for at least 7 days after removal of the drug from the culture medium (Table 6). This substantial level of prolonged inhibition was >99% for I100-15, I100-16 and I100-21 when compared to the p24 antigen levels obtained for untreated HIV-1 infected cells (Table 6). The quantitation of p24 production relative to untreated HIV-1 infected SUP T1 cells for all oligonucleotides tested is presented in Table 6. The presence of sulfur molecules in the backbone of oligonucleotide I100-07 (I100-21) had a more marked effect on the reduction of virus seven days after removal of compound from the culture medium than was observed at the four day post-infection assay point (Table 5).

TABLE 6

Detection of HIV-1 p24 antigen in the culture media of GTO treated SUP T1 cells.

| Oligonucleotide (2.5 uM) | Percent p24[a] | | |
|---|---|---|---|
| | Day 4[b] | Day 7 | Day 11 |
| Control SUP T1 cells | 100.0% | 100.0% | 100.0% |
| I100-07 | 6.0% | 15.9% | 8.6% |
| I100-21 (PT)[d] | 0.0% | 0.0% | 0.0% |
| I100-15 | 0.0% | 0.0% | 0.0% |
| I100-16 | 0.0% | 0.0% | 0.0% |
| I100-18 | 144.5% | 9.7% | 5.3% |
| I100-19 | 208.0% | 21.8% | 15.0% |
| I100-12 (PT) | 0.0% | 0.0% | 0.0% |

[a]Level of detectable p24 in culture medium relative to control (infected but untreated SUP T1 cells after subtraction of background values.
[b]Day 4 post-infection culture medium was replaced with fresh medium without oligonucleotide.
[c]SUP T1 cells infected with HIV-1 but not treated with oligonucleotides or AZT were used as positive control cells in this experiment.
[d]1100-21 and 1100-12 contain phosphorothioate backbone linkages (PT).

In control experiments the culture medium from HIV-1 infected SUP T1 cells treated with AZT (4 $\mu$M) was also replaced on day 4 post-infection with drug free media. In these experiments, two days after removal of AZT from the culture medium the presence of syncytium was observed in the HIV-1 infected cell cultures and by day 4 all cells were visibly infected with HIV-1.

To determine whether the prolonged suppression of HIV-1 was due to toxicity of the oligonucleotides, SUP T1 cells were counted for all treated samples 7 days after removal of the oligonucleotides from the infected cell cultures. The results indicated that for cells treated with 2.5 $\mu$M of drug there was no difference in the number of cells when compared with control cultures (uninfected, untreated) of SUP T1 cells.

Figure 9A:
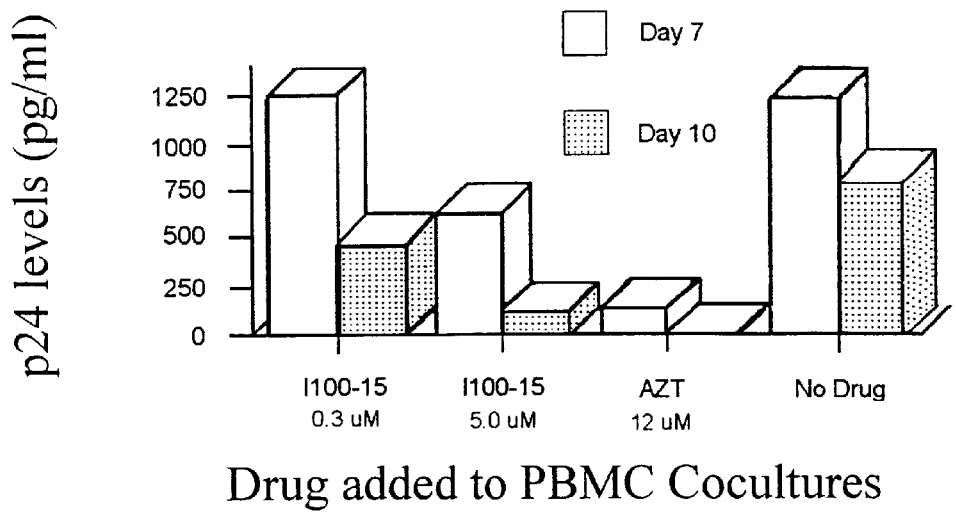
FIG. 9A reveals PBMCs derived from HIV-1 positive patients were mixed with HIV-1 negative PBMCs in culture medium containing drug. On day 7 the cocultures were washed and resuspended in fresh medium containing drug. The p24 levels in medium collected on day 7 (before medium change) and day 10 were assayed for p24.
Figure 9B:
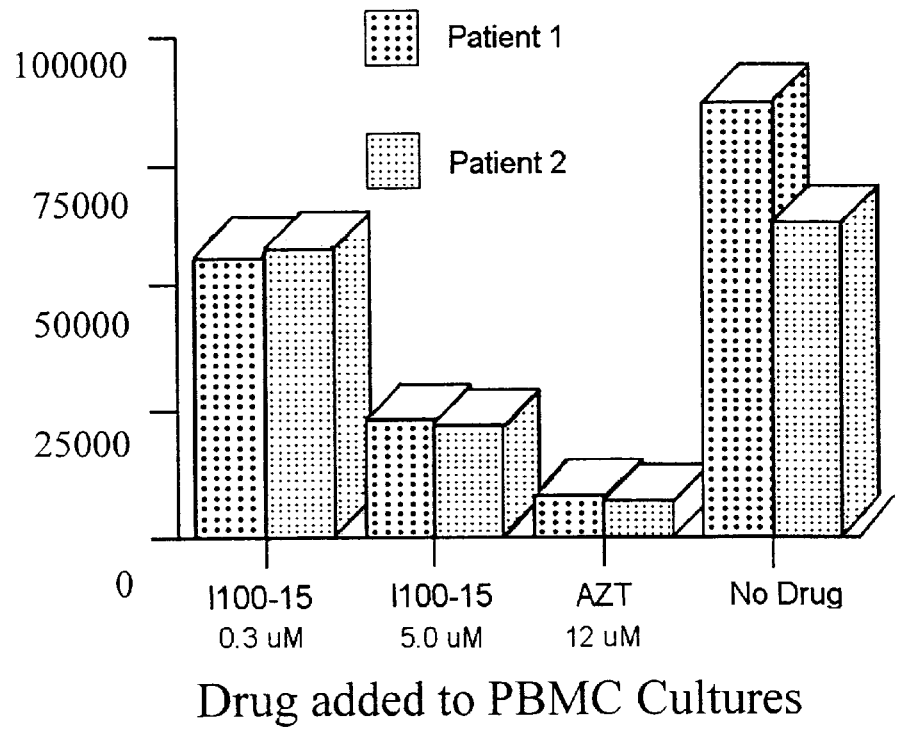

C. Inhibition of HIV expression in patient derived peripheral blood mononuclear cells (PBMCs). I100-15 was assessed for activity in PBMC cultures derived from AIDS patients. Briefly, PHA activated uninfected PBMC's were added to 4PBMC's derived from patients with HIV infection in the presence of varying concentrations of oligonucleotide. Anti-HIV activity was assessed by analyzing supernatants, collected every three days from these mixed cultures, for the presence of HIV p24. The PHA activated PBMC's were grown in the presence of 10 units/ml of IL-1 and medium was exchanged every three days for a period of three weeks. HIV p24 antigen production was assayed in drug-treated as compared to untreated control specimens. It is interesting to note that the results in these experiments (FIG. 9) observed for AZT were obtained when AZT was used at 12 uM which is roughly 300 fold greater than the $ED_{50}$ for this compound.

D. In-Vitro inhibition of HIV-1 reverse transcriptase (RT). The ability of oligonucleotides to inhibit HIV-1 RT in vitro has been well documented. Marshall et al. have described a competitive interaction at the active site as the mechanism by which mono- or diphosphorothioate containing oligonucleotides inhibit HIV-1 RT independent of whether the molecule tested was antisense, a random sequence or poly SdC. To determine whether I100-15 or its parent molecule, I100-07 (or the PT version I100-21), was interacting with HIV-1 RT the activity of this enzyme was assayed in the presence of various concentrations of oligonucleotides. A kinetic analysis of the resultant enzyme inhibition was conducted to determine the mechanism of inhibition. The GTOs appeared to be inhibiting the RNA dependent DNA polymerase activity of the RT enzyme by competitive inhibition at the active site of the enzyme. The $K_i$ value for all of the oligonucleotides tested is presented in Table 7. The data indicate that for all oligonucleotides tested the presence of the sulfur group in the backbone greatly enhanced the interaction between the oligonucleotides and the enzymes. The median inhibitory dose ($ID_{50}$) for these oligonucleotides were also calculated (Table 7). The $ID_{50}$ results are based on the ability of these compounds to inhibit 10 nM of HIV RT.

Short oligonucleotides (18 mers) with PD or PT backbones were assayed to determine whether the nature of the nucleotide sequence contributed to inhibition of HIV-1 RT in this assay system. Comparison of the effects of the PD versions of a GTO (1173 or 1100-15), poly dC (1229) or a random nucleotide sequence (1231) suggested that at this length none of the sequence motifs inhibited RT (Table 7). Other 18 mer PD GTO sequence motifs tested yielded similar results. Enzyme inhibition monitored by both $K_1$ and $ID_{50}$ was observed for the PT versions of these same 18 mer oligonucleotides (Table 7). The degree of enhancement of observed enzyme inhibition for all oligonucleotides tested when the sulfur group was present in the backbone, was between one to three orders of magnitude (Table 7).

TABLE 7

In Vitro Inhibition of HIV-1 RT by PD and PT Oligonucleotides.

| Oligonucleotides | Length | Linkage[b] | Ki ($\mu$M) | ID50 ($\mu$M) |
|---|---|---|---|---|
| I 100-00 | 26 | PD | 0.37 | 5.0 |
| I 100-12 | 26 | PT | 0.005 | 0.015 |
| I 100-07 | 45 | PD | 0.137 | 2.5 |
| I 100-21 | 45 | PT | 0.001 | 0.004 |
| I 100-15 | 17 | PD | >5.0 | >5.0 |
| 1173 | 18 | PD | >5.0 | >5.0 |
| 1174 | 18 | PT | 0.015 | 0.0154 |
| 1229 (poly dC) | 18 | PD | >5.0 | >5.0 |
| 1230 (poly dC) | 18 | PT | 0.044 | 0.033 |
| 1231 (GATC) | 18 | PD | >5.0 | >5.0 |
| 1232 (GATC) | 18 | PT | 0.56 | 0.045 |

[a]Each pair of oligonucleotides contain the same sequence and differ only in the nature of their backbone linkage. Oligonucleotides 1229 and 1230 were poly dC while the 1231 and 1232 oligonucleotides were a random sequence of all four bases (GATC).
[b]The backbone modifications are denoted as PD for phosphodiester and PT for phosphorothioate.

The results from this set of experiments demonstrate that I100-15 is minimally inhibitory to the RNA dependent DNA polymerase activity of HIV-1 RT. The data also indicates that chemically modifying GTOs, poly dC or a random sequence oligonucleotide greatly enhances the in vitro inhibitory activity of the molecule. Therefore, chemically modified oligonucleotides such as the antiviral G-rich molecule describe by Wyatt et al. [112] has by nature a different set of characteristics from oligonucleotides with natural PD backbones.

E. Inhibition of the interaction of HV-1 gp120 with cellular CD4. The outer envelope glycoprotein gp120 of HIV-1 mediates viral attachment to the cell surface glycoprotein CD4 in the initial phase of HIV-1 infection. The effects of both PD and PT modified oligonucleotides on this interaction were examined using a gp120 capture ELISA kit. The concentration of the gp120 used in these studies (125 ng/ml) was determined to be within the linear range of the detection assay. The ability of oligonucleotides to inhibit gp120/CD4 interactions by binding to gp120 was determined by preincubation of the test compounds with soluble gp120 before addition to the immobilized CD4. The results of this experiment (Table 8) are presented as the concentration of oligonucleotide needed to reduce by 50% CD4 bound gp120 ($ID_{50}$ [gp120]). The reciprocal experiment was then performed to measure the ability of the oligonucleotides to inhibit these interactions by binding to immobilized CD4. In this set of experiments I100-00, I100-07 and the PT versions of these two oligonucleotides were capable of preventing the interaction of gp120 with immobilized CD4 ($ID_{50}$ [CD4], Table 8). For both sequences tested, the PT version of the oligonucleotide the $ID_{50}$ values were 50 to 100 fold lower than with the PD version.

A fixed length (18 mer) set of oligonucleotides with either PD or PT backbones were assayed to determine whether the nature of the nucleotide sequence contributed to inhibition of gp120/CD4 interactions. As was observed for the inhibition of HIV-1 RT, the PD versions of these molecules had little to no measurable effects on the binding of gp120 with CD4. However, the PT versions of these oligonucleotides did yield measurable inhibitory activity. The 18 mer GTO (1174) interrupted gp120/CD4 interactions at approximately 10 fold lower concentrations than poly $(SdC)_{18}$ (1230) while the random sequence 18 mer (1232) had no measurable activity (Table 7).

TABLE 8

In Vitro Inhibition of HIV-1 gp120 Interaction with CD4 by PD and PT Oligonucleotides.

| Oligonucleotide | Linkage[a] | ID50 [gp120]($\mu$M) | ID50[CD4]($\mu$M) |
|---|---|---|---|
| I 100-00 | PD | 3.50 | 18 |
| I 100-12 | PT | 0.08 | 0.475 |
| I 100-07 | PD | 0.80 | 4.25 |
| I 100-21 | PT | 0.07 | 0.048 |
| 1173 | PD | >100 | >100 |
| 1174 | PT | 0.09 | 0.45 |
| 1229 (poly dC) | PD | >100 | >100 |
| 1230 (poly dC) | PT | 1.00 | 3.25 |
| 1231 (GATC) | PD | >100 | >50 |
| 1232 (GATC) | PT | >10 | >10 |

[a]Each pair of oligonucleotides contain the same sequence and differ only in the nature of their backbone linkage.
[b]The backbone modifications are denoted as PD for phosphodiester and PT for phosphorothioate.

F. Oligonucleotide interactions with the v3 loop of HIV-1 gp120. It has been reported previously that poly SdC oligonucleotides were able to bind to the third variable loop domain of HIV-1 gp120 (v3 loop). The degree of interaction was reported to be dependent on the length of the oligonucleotide studied, with a rapid decrease in binding affinity observed for compounds shorter than 18 nucleotides. The detection antibody used to monitor inhibition of gp120/CD4 interactions in the capture gp120 ELISA KIT (HRP-α-GP120) used in this study (Table 8) recognized an epitope in the gp120 v3 loop (manufacturer's information). For this reason control experiments were performed to determine whether the observed inhibition of gp120/CD4 interactions was due in part, or in whole, to interference with the HRP-α-gp120 detection antibody. The results indicated that I100-07 and I173 (PD backbones) did not inhibit the detection of immobilized gp120 however, the PT oligonucleotides tested (I100-21 and 1174) were able to slightly inhibit the detection of gp120 at oligonucleotide concentrations above 5 $\mu$M. This level of inhibition was too small to account for the $ID_{50}$ [gp120] values presented for I100-21 and 1174 in Table 8.

Figure 10A:
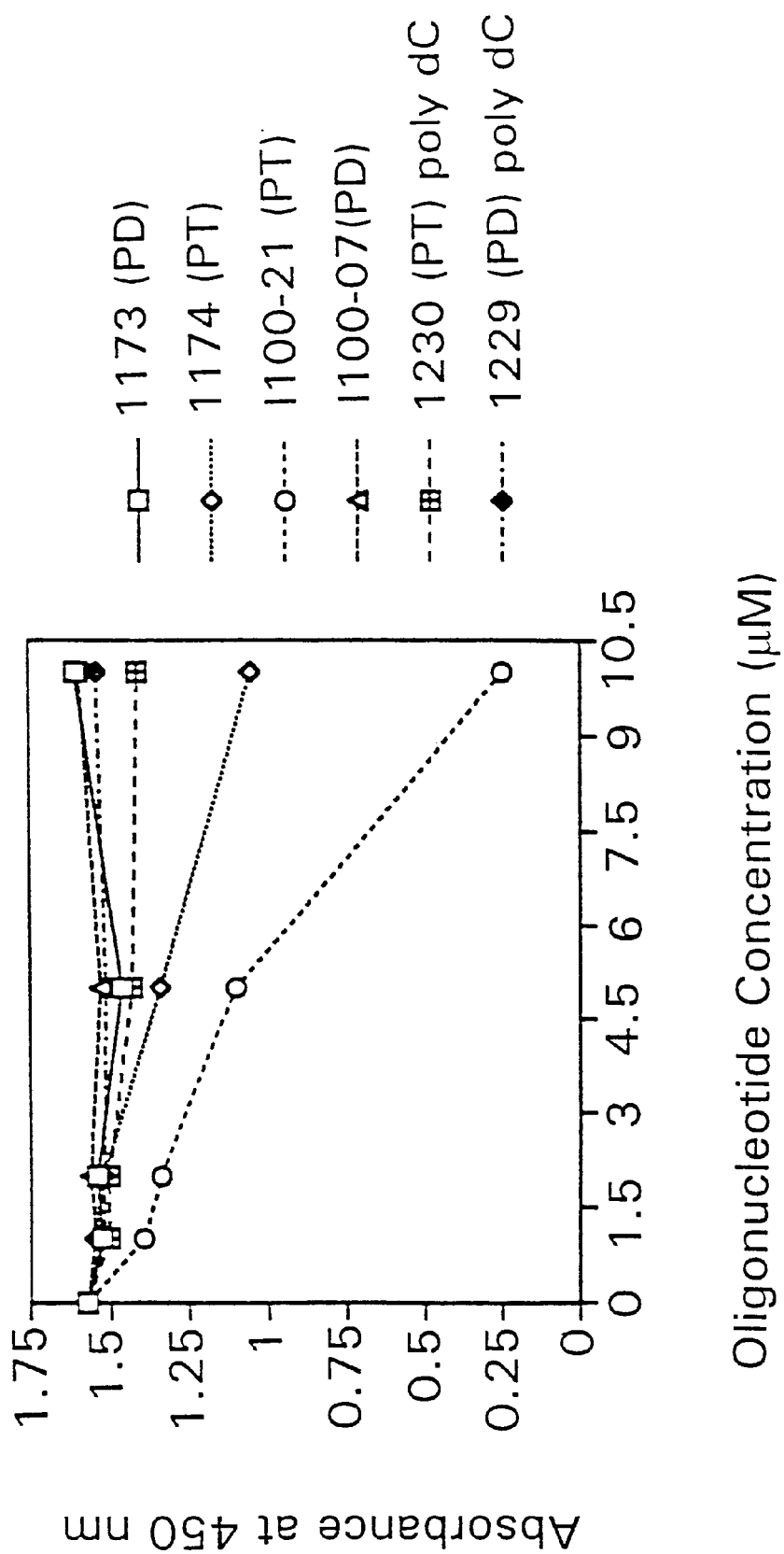
FIGS. 10A and 10B show inhibition of binding of V3 loop specific Mabs to HIV-1 gp120 by phosphorothioate containing oligonucleotides. Matched sequence oligonucleotides with either phosphodiester (PD) or phosphorothioate (PT) backbones were assayed for their ability to inhibit the interaction of V3 loop specific Mabs with the gp120 molecule: SEQ. ID. NOs. 31 (1173) and 32 (1174); SEQ ID. NOs. 24 (I100-07) and 39 (I100-21); or SEQ. ID. NOs. 42 (1229) and 43 (1230). To do this, immobilized gp120 was preincubated with oligonucleotides before washing and the addition of Mab NEA 9284 (panel A) or Mab NEA 9301 (panel B).
Figure 10B:
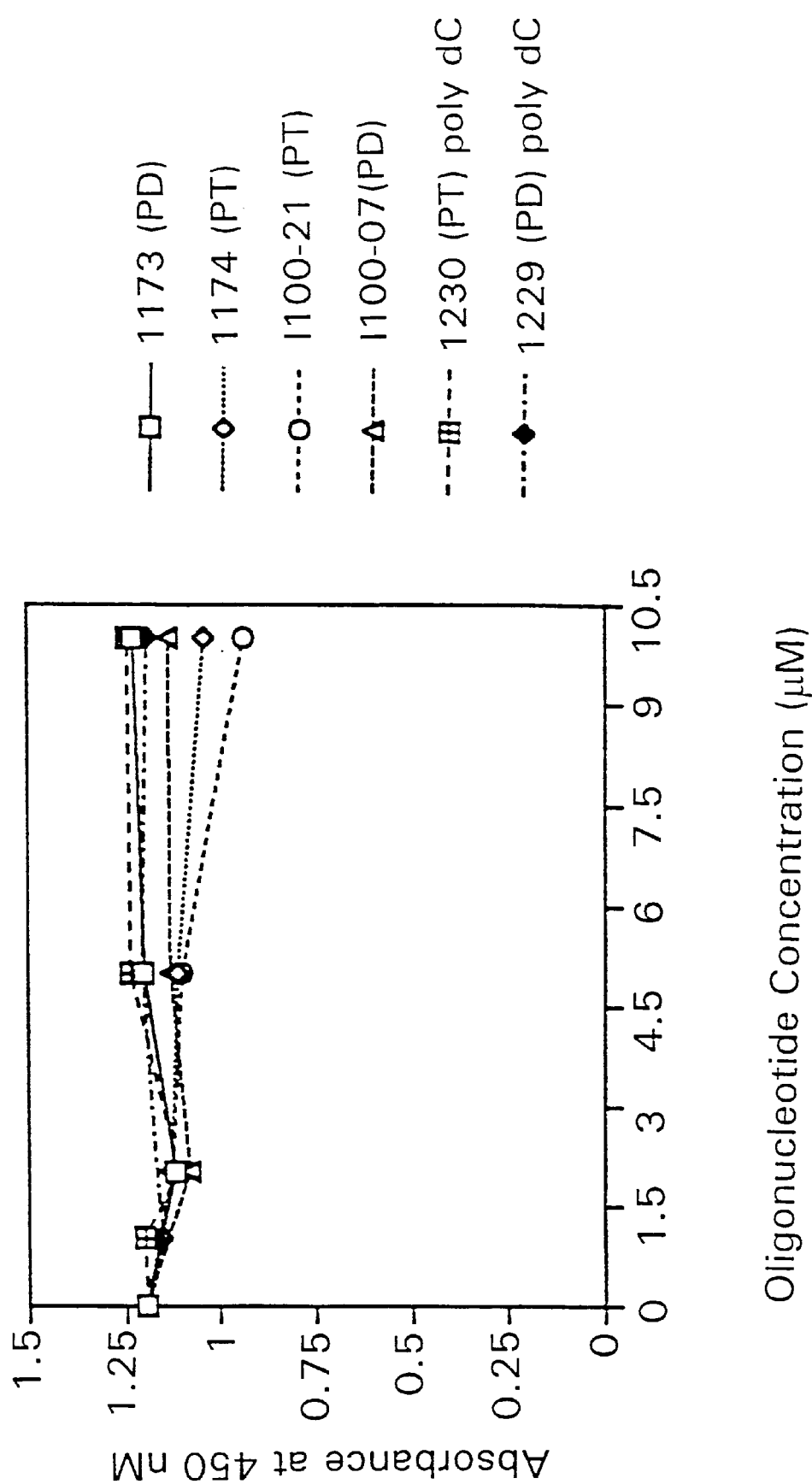

Further analysis of oligonucleotide interactions with the v3 loop was conducted using a v3 loop specific murine Mab, NEA-9284 (FIG. 10). PT oligonucleotides were able to inhibit binding of NEA-9284 to gp120. The presence of bound gp120 specific Mab was determined using a HRP-labeled goat-α-mouse antibody. The results of these experiments indicate that PT oligonucleotides were able to inhibit binding of NEA-9284 to gp120. The $ID_{50}$ for the most active oligonucleotide (I100-21) was approximately 4 to 7 $\mu$M. This concentration is approximately 10 to 30 fold higher than the $ED_{50}$ for this oligonucleotide against HIV-1 in culture (Table 8). The PD oligonucleotides tested did not inhibit the binding of any Mab to gp120 therefore, it is unlikely that this is the mechanism by which the PD GTOs such as I100-07 (and hence I100-15) are inhibiting HIV-1.

Figures 11A, 11B:
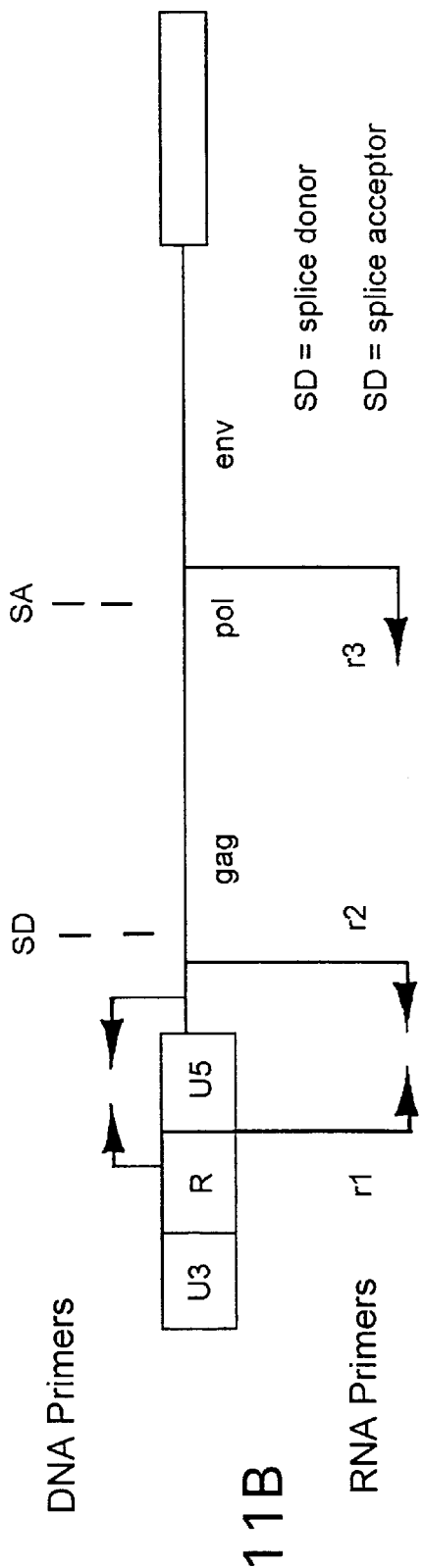
FIG. 11 shows a schematic diagram of the HIV-1 genome not drawn to scale.

G. Analysis of HIV-1 RNA and DNA in single cycle assays. Total RNA and DNA were extracted from SUP T1 cells 36 hours after infection with 0.1 m.o.i of HIV-1$_{DV}$. In this assay the infected cells were treated with I100-15 or AZT at various time points before, during or after infection. Harvesting of the infected cells at 36 hr post-infection allowed for the analysis of approximately one round of viral replication. A schematic diagram of the positions of the PCR primers used in the DNA and RNA analysis is shown in FIG. 11.

Figure 12:
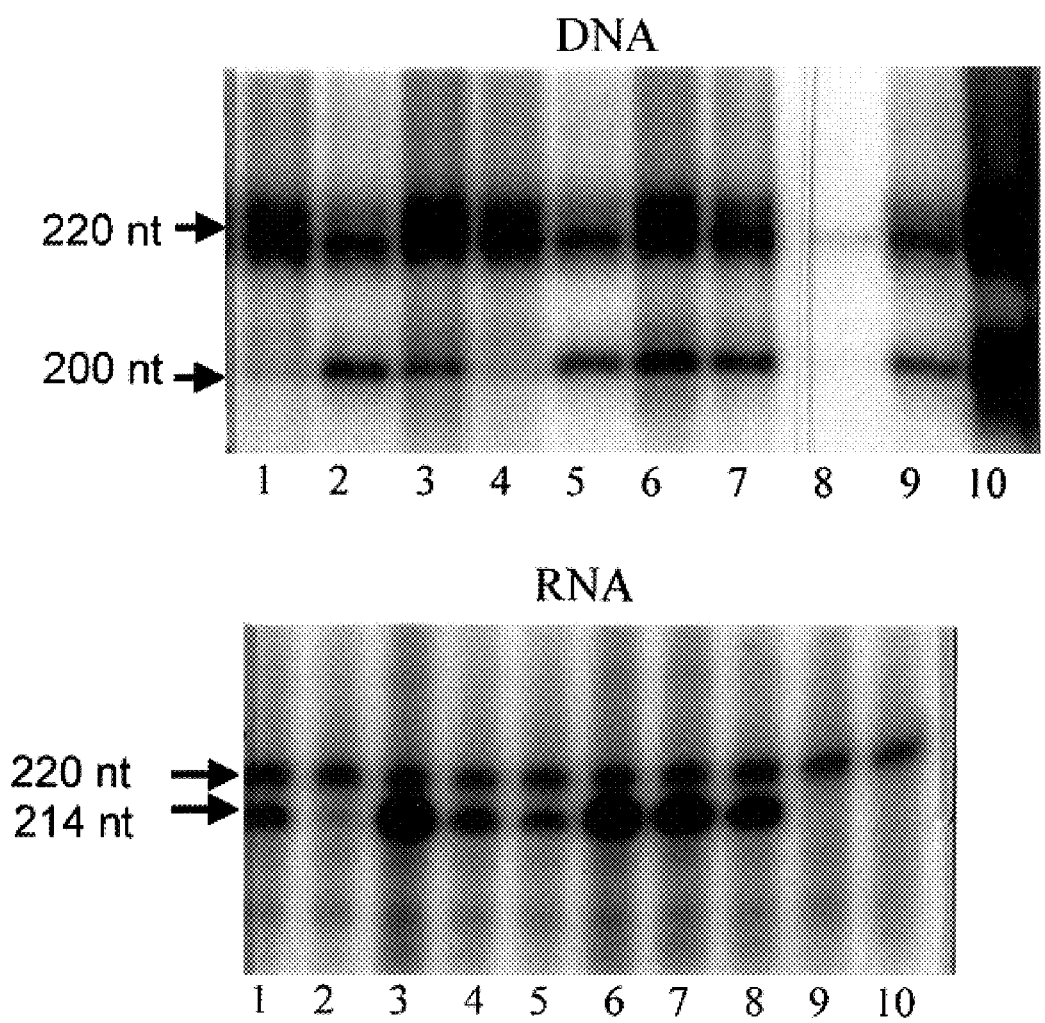
FIG. 12 shows analysis of DNA (PCR) and RNA (RT-PCR) extracted from SUP T1 cells three days post-infection with HIV-1. (Left Panel). PCR analysis of HIV-1 infected drug treated SUP T1 cell DNA used 0.1 µg of total extracted DNA for each reaction. In this experiment either AZT, at 0.3 µM which is 10 fold over the $ED_{50}$ value (lane 1) or I100-15 at 5.0 (lane 2) or 0.3 µM (lane 3) were added to SUP T1 cells at the same time as HIV-1. Lanes 4 (AZT), 5 (5.0 µM I100-15) and 6(0.3 µM I100-15) are the results of DNA samples obtained from cells in which drug was added 8 hours post-infection. Lanes 8 to 10 contain 10, 100 or 1000 ng of DNA extracted from HIV-1 infected control SUP T1 cells. The band corresponding to 220 bp is the predicted size of the internal β-actin control and the 200 bp fragment is the predicted size for the amplified portion of the HIV-1 genome. The right panel contains RT-PCR analysis of extracted RNA (1 µg/reaction) obtained from cells treated in an identical fashion as those described in lanes 1–6 of the left panel. Lanes 7 and 8 are control HIV-1 infected cell mRNA and lanes 9 and 10 are the results obtained using uninfected untreated SUP T1 cell mRNA.

Total extracted DNA was analyzed using a PCR primer set which would amplify a 200 bp portion of the viral genome spanning the repeat element (R) into the gag gene. The primer set detected full-length or nearly completely synthesized viral DNA. This is the last region of the minus strand of viral DNA that is synthesized. Thus, for DNA to be detected by this primer set, two template-switching events have occurred and contiguous 5'LTR to gag sequences must be present on either the minus or plus strand of DNA. In the same reaction mixture a PCR primer set which would amplify a 220 bp region of the human b-actin gene was used. The results indicate that in cells treated with AZT there was a marked decrease in viral DNA synthesis when the drug was added up to 4 hrs post-infection as expected (data in FIG. 12 shows zero hour and 8 hour time of addition studies). The effects of I100-15 on the early rounds of viral DNA synthesis was minimal. The results of this experiment indicate that I100-15 did not inhibit virus entry into the cells because of the detectable levels of viral DNA even in samples treated with I100-15 at the same time as virus infection (zero hour addition). Furthermore, it suggests that I100-15 has a different mechanism of action compared to AZT.

Additional experiments using alternative PCR primers, suggest that there may be alterations in the viral DNA synthesis caused by I100-15. The observed amplification products, when primers clustered in the U3 region of the virus were used, yielded a banding pattern which was not predicted and obviously different from the infected cell control (untreated) and the AZT treated infected cell samples.

RNA extracted from HIV-1 infected cells was analyzed by RT-PCR. In this assay the antisense primer of the PCR primer pairs is used with MMLV RT and extracted mRNA to synthesize cDNA strand. This cDNA is then used as templates in PCR reactions. Two RNA primer sets were used to analyze unspliced (primers r1 and r2) and spliced (primers r1 and r3) HIV-1 transcripts. Predicted sizes of the amplified products were 101 bp and 214 bp for the unspliced and spliced species respectively. The same β-action primers used for the analysis of the DNA samples were used as controls in this experiment. The results obtained using primer pair r1 and r3 are depicted in FIG. 12 above. The results of this experiment clearly indicate that a reduced level of HIV-1 specific transcript was observed in samples treated with I100-15 in the samples treated with drug at the same time as virus infection (zero hours). It is also clear that while samples treated with AZT had reduced levels of viral cDNA, viral mRNA was still being produced.

The same decrease in HIV-1 specific transcript was observed in viral infected cells treated with I100-15 when the r1 and r2 primer pair was used (data not shown).

H. Structural analysis of I100-15 and I100-26. I100-07, and its derivative products including I100-15 and I100-26, are composed entirely of deoxyguanosine (G) and deoxythymidine (T). These G-rich oligonucleotides were purified using anion exchange reverse phase HPLC. Using this procedure the oligonucleotide is purified in the presence of sodium ions. Monovalent cations are known to encourage self-associated structures for G-rich molecules, all of which involve formation of G-tetrads. The G-tetrad formation involves the formation of eight hydrogen bonds by coordination of the four $O^6$ atoms of guanine with alkali cations believed to bind to the center of a quadruplex, and by strong stacking interactions. The oligonucleotides purified using anion exchange chromatography then have an opportunity to form inter-or intramolecular tetrads. The tetrad structure can be strengthened by replacing the sodium ion with potassium.

Figure 13:
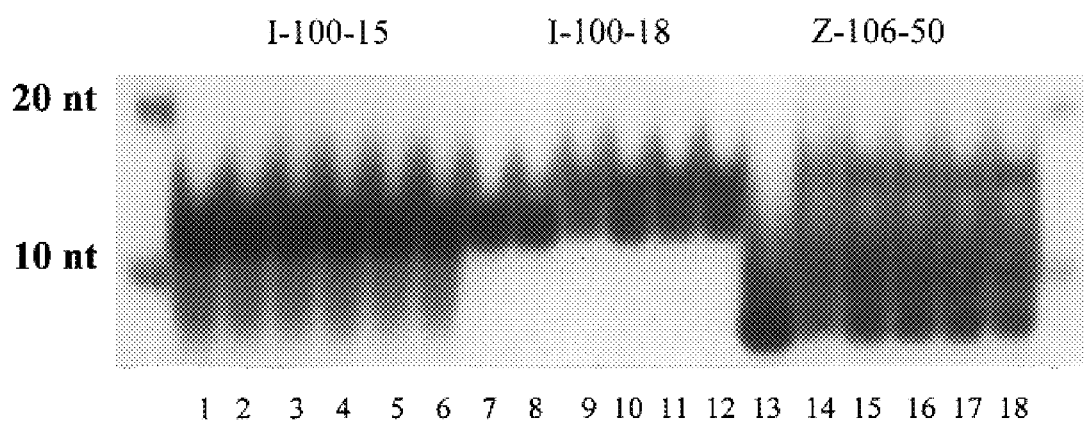
FIG. 13 shows the results of three oligonucleotides (10$^{-5}$M) incubated with increasing concentrations (0,7.5,15,30, 60 and 120 mM) of KCl (lanes 1–6 for I100-15, 7–12 for I100-18 and 13–18 for Z106-50). The nucleotide markers are poly dT.
Figure 14:
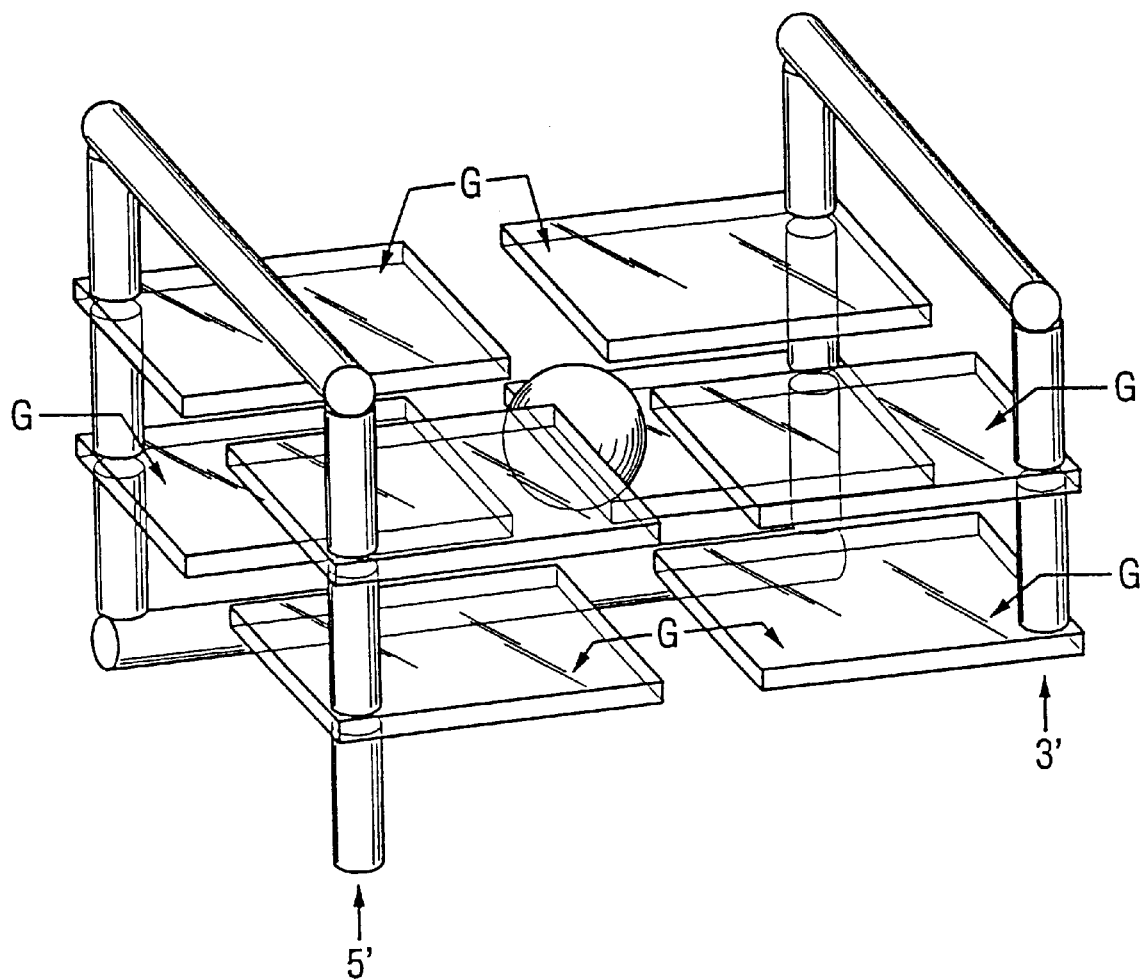
FIG. 14 shows a line model for I100-15. A line model of I100-15 folded into an intramolecular tetrad of the Oxytricha class is depicted. The 5'-end of the molecule is in the bottom left hand side. The bases (Gs) are stacked on top of each other with the 4 bases in each plane stabilized through their hydrogen bonding with each other and their interaction with the K$^+$ ion complex in the center of the tetrad.

I. Nondenaturing gel analysis. I100-15 (17 mer, Table 5) was analyzed using nondenaturing polyacrylamide gel electrophoresis. In this experiment, trace concentrations of radiolabeled oligonucleotide ($10^{-7}$M) was incubated with increasing concentrations of cold oligonucleotide (up to $10_{-5}$M) before gel analysis in the presence of monovalent cation. Under the gel conditions used I100-15 migrated as a unique band faster than a random coiled (denatured) 17 mer oligonucleotide would as and did so in a concentration independent fashion (data not shown). This is in contrast to I100-18 (16 mer, Table 52 10 fold less active than I100-15) which appeared to migrate as multiple species in a concentration dependent fashion under the same gel conditions (data not shown). The same phenomena was observed when $10^{-5}$ oligonucleotide (total cold and radiolabeled oligonucleotide) was incubated with increasing concentration of KCl (FIG. 13). I100-15 migrated as a unique species at all concentrations of KCl while I100-18 and Z106-50 (ggttggggttggg) migrated as multiple species.

The results from these assay suggests that I100-15 folds into an intramolecular structure while other G-rich oligonucleotides such as I100-18 and Z106-50 aggregate into higher order intermolecular structures. It is interesting to note that the PT G-rich compound described by Wyatt et al., P.N.A.S. 1994 91:1356–66, with the sequence $T_2G_4T_2$, was claimed to fold into an intermolecular tetrad. Therefore, I100-15 (PD backbone) is structurally and chemically different from ISIS PT oligonucleotide.

J. Tetrad Structure. Principally due to its role in telomere formation, the structure of four stranded nucleic acid tetrads has been well studied. Most eukaryotes possess a repeating G-rich sequence of the form (T/C)nGm where n=1–4 and m=1–8. Of particular interest to the study of the I100-15 class of GTO is the structure of the telomere sequence repeat $T_2G_4$, first detected in Oxytricha. The oxytricha repeat has been studied in oligonucleotides by NRM, Smith et al., Nature et al, Nature 1992, 356:164–68, and by crystallographic methods, Kang et al. Nature, 1992 356:126–31. As had been predicted from numerous previous physical and biochemical studies, both the NMR and crystallographic studies suggest that folding is mediated by square planar Hoogsteen H-bonding among G residues, with overall antiparallel orientation of the four strand equivalents comprising the tetrad fold. As expected, the crystallography has shown that the structure is selectively stabilized by tight binding of a small monovalent cation to the $O^6$ oxygen of guanosine. But surprisingly, both NMR and crystallography confirm that the folded structure possess alternating syn/anti glycosidic bond angles (as opposed to all anti for most duplex structures).

Feigon and colleagues have used NMR and modelling to deduce the structure of a 28 base-long oligonucleotide $(G_4T_4G_4T_4G_4T_4G_4$, Oxy 3.5) which is capable of forming a well-defined all-antiparallel intramolecular tetrad, Smith et al., Nature 1992 356:164–68. If the GTO I100-15 were to fold to form a stable intramolecular tetrad its NMR properties would be expected to be similar to those of the Oxy 3.5 molecule. In the folded state, the salient NMR characteristics of the intramolecular Oxy 3.5 tetrad were as follows:

1. Narrow linewidths, indicative of monomer formation only.
2. Induction of well-defined guanosine N1 Hoogsteen imino resonances in the 11.2 to 11.7 ppm range. The chemical exchange rate of these protons is very slow, reflective of the high positive cooperativity of tetrad folding and dissociation.
3. Spectral simplicity, indicative of a single predominant folded structure, rather than an equilibrium among different folded structures.
4. Intrabase H8-C1' and interbase H7-C2" NOE connectivity which demands a pattern of alternating syn-anti glycosidic bond angle throughout the "tetrad stem" of the folded structure.

Figure 15:
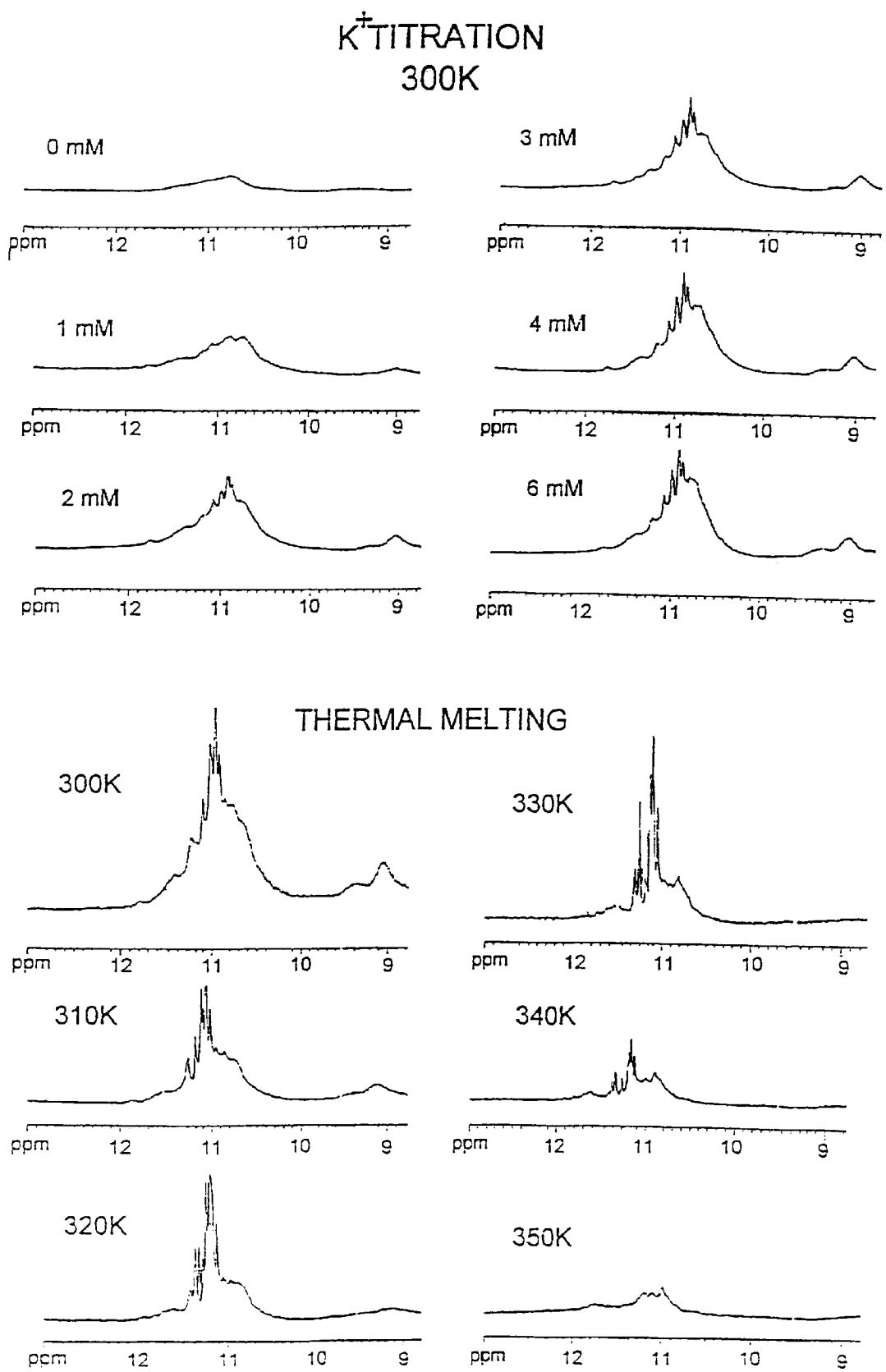
FIG. 15 displays a KCl titration.

K. One dimensional NMR analysis. Displayed in FIG. 15 is a line model for I100-15, folded to form an intramolecular tetrad of the Oxytricha class. From a physical perspective, the possibility that an intramolecular tetrad structure might form in high KCl or NaCl is not surprising. What is surprising is the fact that this model proposes a stem region comprising a single G-octet and intervening loop regions which are only two bases long.

In order to test the general feasibility of this model, a detailed 3D molecular model for a I100-15 has been constructed. In this we have assumed that the 8 G's comprising the octet core of the structure form a standard square planar octet, and that glycosidic angles are as in the crystal and NMR structures of the antiparallel Oxytricha tetrads, Smith et al., Nature 1992 356:164–68, and Kang et al., Nature 1992 356:126–31. Additionally, a single $K^+$ ion has been introduced into the center of the G-octet, with octahedral coordination to $GO_6$. Initially, 2 base loop structures were created so as to connect elements of the octet without disruption. Subsequent to this initial guess, the structure was subjected to mechanical refinement with full electrostatics, employing Charmm parameters in Sybyl.

After refinement, it was observed that coordinates of the octet core were not significantly altered and that backbone parameters within the loop domains were within acceptable energetic limits.

First, the structure is very compact, nearly spherical, with the three loop regions and the 5' "GT tail" comprising the surface of the tetrad core. Based upon this structure, it appears likely that interaction with cellular macromolecules will be heavily dominated by the structures of these surface loops. In that regard, it may be inappropriate to think of such interactions as "tetrad binding." The inclusion of G-tetrads in such a structure may not be important as a recognition element per se, but instead provides a latticework upon which an orderly loop array is positioned.

Further, although the loop regions do not appear to be under mechanical stress, they are short enough so that they possess very configurational freedom. Because of those severe length constraints, we have found that all feasible loop models display a distinct "rabbit ears" structure, wherein the two base planes of the loop region are unstacked, and point outward from the center of the octet core. Such rigid, unstacked, single strand loop character is very distinctive as compared to other known folded nucleic acid structures. Therefore, varying the sequence or chemical structure of these loops, one at a time, is necessary to determine if bonding interactions between these loops and cellular macromolecules are important to the observed anti-HIV activity.

The structures described above possess a single G-octet core, which is known to be the minimum structure required for nucleation of tetrad formation. Therefore, when paired with the observed short loop size, the intramolecular tetrad structure proposed for I100-15 is best described as metastable, relative to other more robust tetrads which have been described in the literature. An increase of the core from 2 to 3 stacked tetrads, or an increase in the length of flexibility of one or more loops would be expected to increase the thermodynamic and/or kinetic stability of this structure significantly. Thus, the observed anti-HIV activity can be improved by sequence modification which enhances the stability of the underlying tetrad latticework.

Finally, it has been observed that I100-15 and homologues display profound resistance to cellular nucleases. One interesting aspect of the proposed structure is that, even in the loop domains, phosphodiester linkages (red) are generally buried from interaction with large solutes, such as a nuclease. The structure analysis proposed defines local phosphodiester backbone structure at low resolution. When paired with explicit biochemical analysis of phosphodiester cleavage rate, it is possible to define sites for selective introduction of backbone modification in I100-15 homologies, for the purpose of extending the biological half life in vivo.

The gel electrophoresis data described above suggests that I100-15 spends every little time as a random coil at 25° C., under native salt conditions. Although the gel data rules out intermolecular associations, the data do not constrain the oligomer to any particular folded monomeric structure. Oligonucleotide folding in I100-15 has been studied employing a combination of high resolution NMR and methods.

Stable formation of a discrete octet core, mediated by tight binding of a single monovalent ion is crucial to the model described above. Given that G-N1 imino protons give rise to sharp, characteristic $^1H$ NMR signals in such a structure, focus has been on the potassium ion dependence and temperature dependence of I100-15 folding, as assessed by $^1H$ NMR at 500 mHz.

For these measurements, I100-15 has been synthesized at 15 uM scale employing fast deblocking "Expedite" chemistry on a Milligen synthesizer. Subsequent to purification by denaturing anion-exchange chromatography in base (10 mM LiOH, 0.2 to 0.7M NaCl), oligomer purity was confirmed by denaturing gel electrophoresis (7M urea, 65° C.). For NMR, the oligomer was desalted and transferred into 20 mM LiCl adjusted to pH 6.0, which minimizes folding to form tetrads. Oligonucleotide strand concentration was held constant at 2.7 mM. MMR was measured in $H_{2O}$, employing a Redfield pulse sequence to saturate the water resonance, as described previously, Dittrich et al., Biochemistry, 1994, in press.

In FIG. 16 a KCl titatation is displayed. At 300° K., in the absence of added $K^+$, imino proton signals cannot be resolved in the 10–12 ppm region. Subsequent to addition of KCl, substantial narrowing of imino signals is obtained, saturating at an added KCl concentration of 3 mM, which is very close to one added $K^+$ equivalent per octet. Above 4 mM it can be seen that at least two classes of imino resonance can be detected in the 10–12 ppm range with roughly equal intensity: a broad envelope from 10–11 ppm, upon which several sharp resonances are superimposed in the 11–11.5 ppm region.

By analogy with chemical shifts of other G tetrad structures, we tentatively ascribe the sharp imino signals to the 8 Hoogsteen H bonds of the core octet. The broad envelope is ascribed to the G and T imino resonances contributed by the loop and 5' terminal domains. Consistent with published tetrad NMR data, a broad envelop of signal was detected at 9 ppm, which most likely results from unusually show exchange of guanosine N2 protons engaged in Hoogsteen pairing.

In order to better distinguish the two classes of imino $^1H$ signal and, additionally, to investigate the gross stability characteristics of the folded 1100-15 structure, thermal melting analysis, at 2.7 mM in strands, 6 mM KCl, 20 mM LiCl, pH 6.0 over the range from 300° K. to 345° K. has been performed.

Substantial line narrowing of "Hoogsteen" imino proton signals is seen at 310° K., which appears to be accompanied by broadening of the poorly resolved imino envelope at 10.7 ppm. This narrowing plateaus above 310° K., giving rise to 7–8 well-resolved imino protons at 320° K. By reference to the NMR behavior of the oxytricia tetrad and other tetrad structures, the formation of 7 to 8 narrow,well-resolved imino resonances at elevated temperatures strongly suggests that in the presence of one bound $K^+$ ion per octet equivalent, 1100-15 has folded into a discreet tetrad structure, stabilized by the 8 Hoogsteen H-bonds of the presumed octet.

In the range from 330 to 340° K., the imino proton spectrum undergoes an abrupt transition, which is likely to be representative of cooperative unfolding of the octet. Stability of this kind, accompanied by apparently high thermal cooperativity is very striking indeed, and is generally indicative of a single, well-defined folded oligonucleotide structure.

The origin of the shallow temperature dependence of the spectral parameters, leading to enhanced $^1H$ resolution at 320° K., remains to be determined. It is likely to have resulted from weak intermolecular association which occur in the millimolar strand concentration range. This interpretation is born out by preliminary analysis of spectral parameters as a function of strand concentration (not shown). Independent of interpretation, the data suggests that high quality NMR data may be obtained for exchangeable and non-exchangeable I100-15 protons at 35° C., 20 mM, LiCl, 6 mM KCl and 2 mM in strand equivalents.

EXAMPLE 11

INHIBITION OF HCMV ACTIVITY

Several different oligonucleotides reduced HCMV titers in tissue culture. Each of the oligonucleotides contained a different percentage of guanosine residues and a different number of total nucleotides in the polymer. The results of this assay are depicted in Table 9. All oligonucleotides were capable of reducing viral titer in culture including G101-50 which contained only 53% G residues (16 out of 30 total nucleotides). In Table 9, the length and percent guanosine nucleotides is indicated for each oligonucleotide tested.

TABLE 9

Oligonucleotide Inhibition of HCMV Activity
Viral Yield in plaque forming units (PFU)
oligonucleotide (% G)

| [oligo] | G101-50 (53%) 30 mer | G105-50 (80%) 31 mer | G106-50 (78%) 27 mer | G109-50 (65%) 29 mer | G113-50 (64%) 24 mer |
|---|---|---|---|---|---|
| None | $4.5 \times 10^3$ PFU | $4.5 \times 10^3$ PFU | $4.5 \times 10^3$ PFU | $4.5 \times 10^3$ PFU | $4.5 \times 10^3$ PFU |
| 20.0 μM | Ø | $4.5 \times 10^1$ PFU | $2.5 \times 10^1$ PFU | $8.0 \times 10^1$ PFU | $3.5 \times 10^1$ PFU |
| 10.0 μM | $2.5 \times 10^1$ PFU | $1.8 \times 10^2$ PFU | $4.0 \times 10^1$ PFU | $4.5 \times 10^1$ PFU | $4.0 \times 10^1$ PFU |
| 1.0 μM | $7.0 \times 10^2$ PFU | $1.9 \times 10^2$ PFU | $6.0 \times 10^1$ PFU | $1.5 \times 10^2$ PFU | $5.0 \times 10^2$ PFU |
| 0.5 μM | $8.0 \times 10^2$ PFU | $2.7 \times 10^2$ PFU | $1.3 \times 10^2$ PFU | $3.0 \times 10^2$ PFU | $5.4 \times 10^{2-}$ PFU |

In NIH3T3 cells chronically infected with FMLV, oligonucleotides (FIG. 1) were capable of inhibiting virus production. However, oligonucleotides controls in this experiment were capable of inhibiting virus production in culture.

EXAMPLE 12

IN VITRO ENZYMATIC ASSAYS

Figure 4:
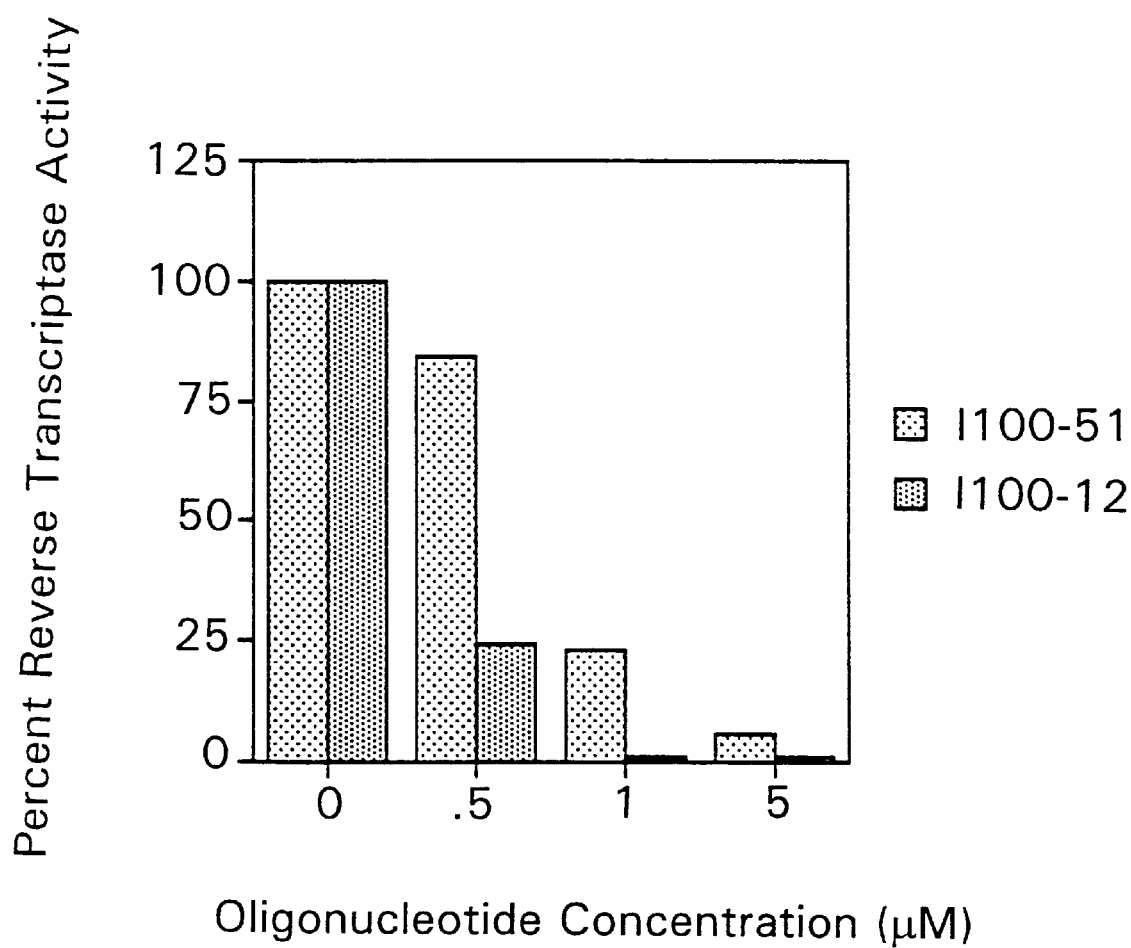
FIG. 4 shows the culture media taken from NIH3T3 cells chronically infected with FMLV was mixed with various concentrations of I100-51 or I100-12 (fully phosphorothioate version of I100-00). The mixtures were then assayed for the presence of viral reverse transcriptase. The data is presented as a percent of measurable reverse transcriptase in culture medium not treated with oligonucleotide.

Culture media containing FMLV reverse transcriptase (RT) was mixed with various concentrations of I100-51 or I100-12, the phosphodiester backbone of I100-51 having been modified to a phosphorothioate backbone. Reverse transcriptase was measured as described in Example 7. FIG. 4 shows that both oligonucleotides were capable of inhibiting the RT enzyme. Inhibitory concentrations for 50% reduction in RT activity was between 0.5 to 1 μM for I100-51 and less than 0.5 uM for I100-12.

Figure 5A:
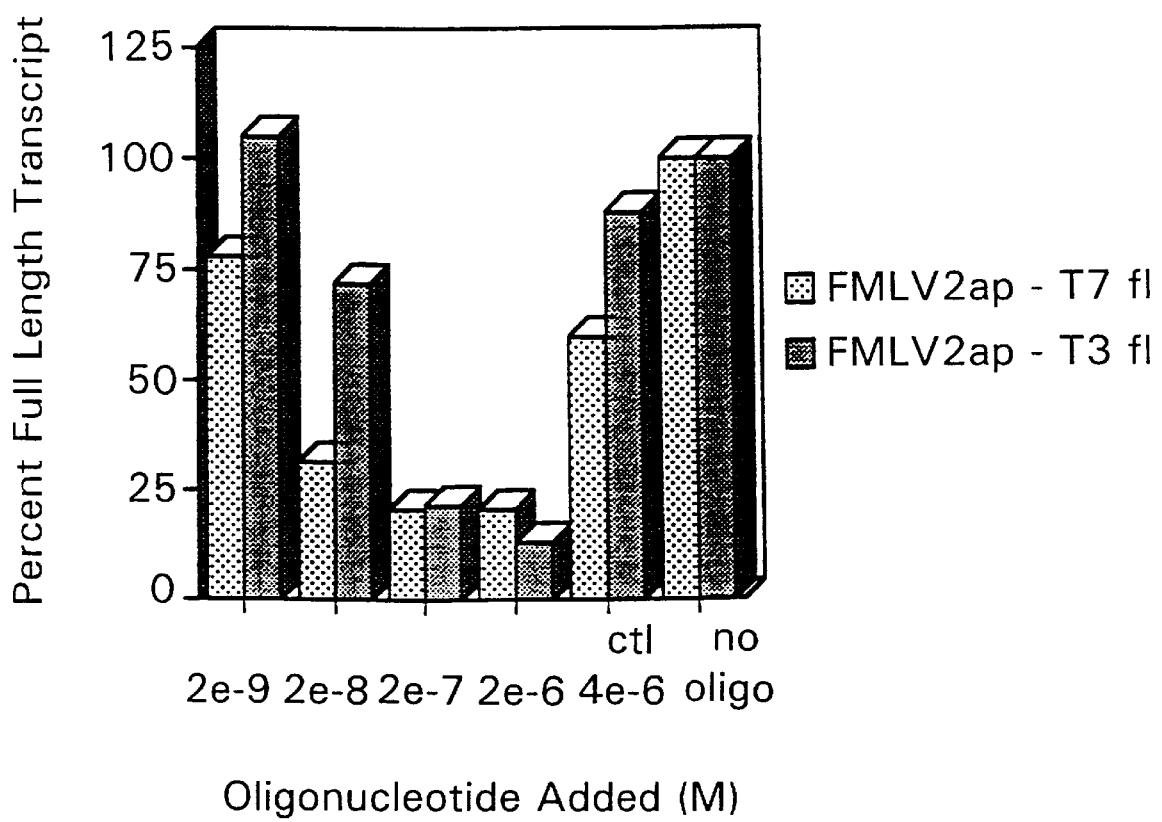
FIGS. 5A, 5B and 5C show the radio-labelled ($^{32}$P) full-length or truncated mRNA transcripts were analyzed by polyacrylamide gel electrophoresis, and then quantitated by cutting out the specific transcript and measuring the radioactivity in a scintillation counter.
Figure 5B:
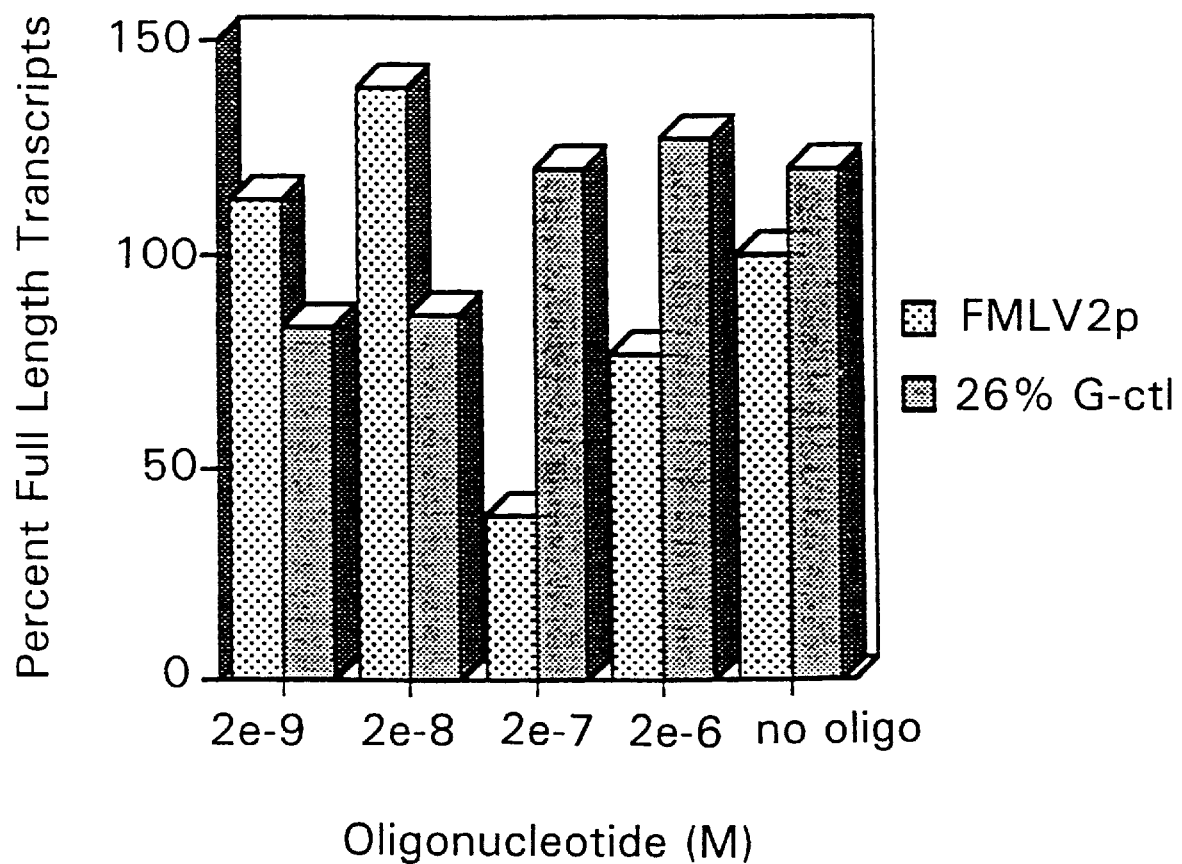
Figure 5C:
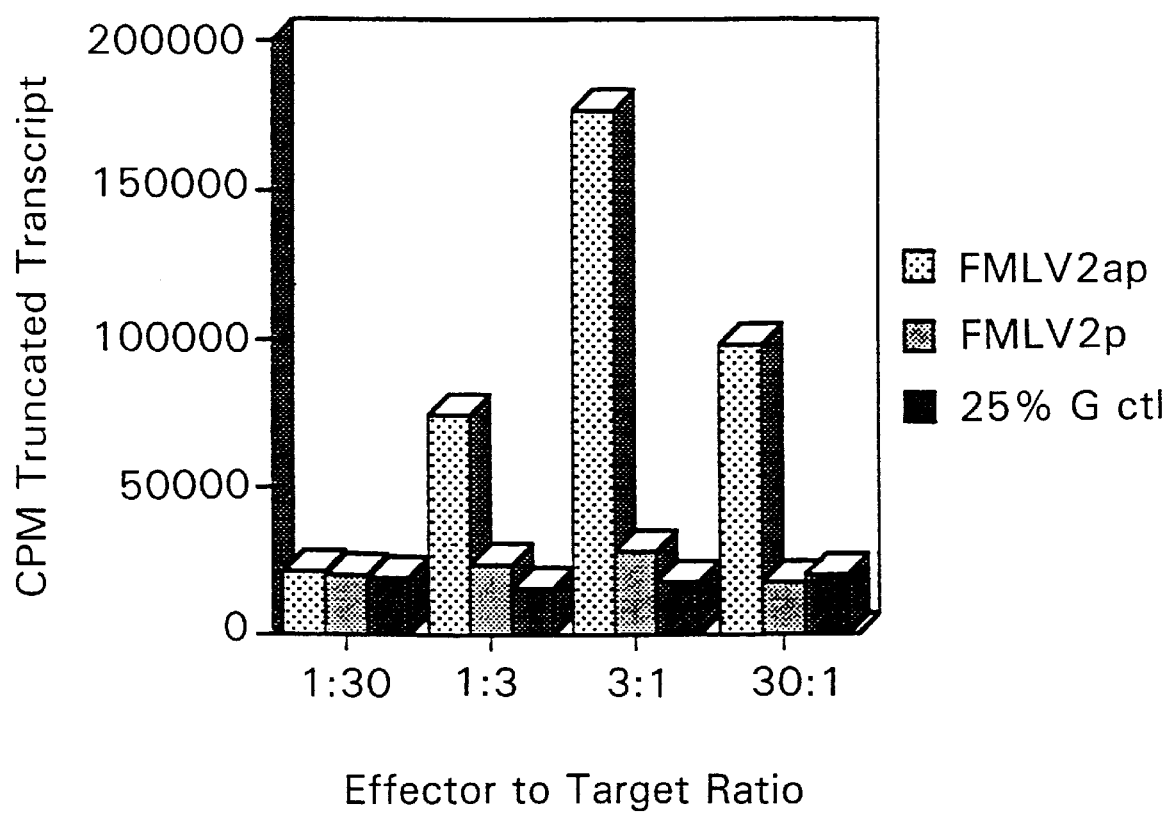
Figure 6:
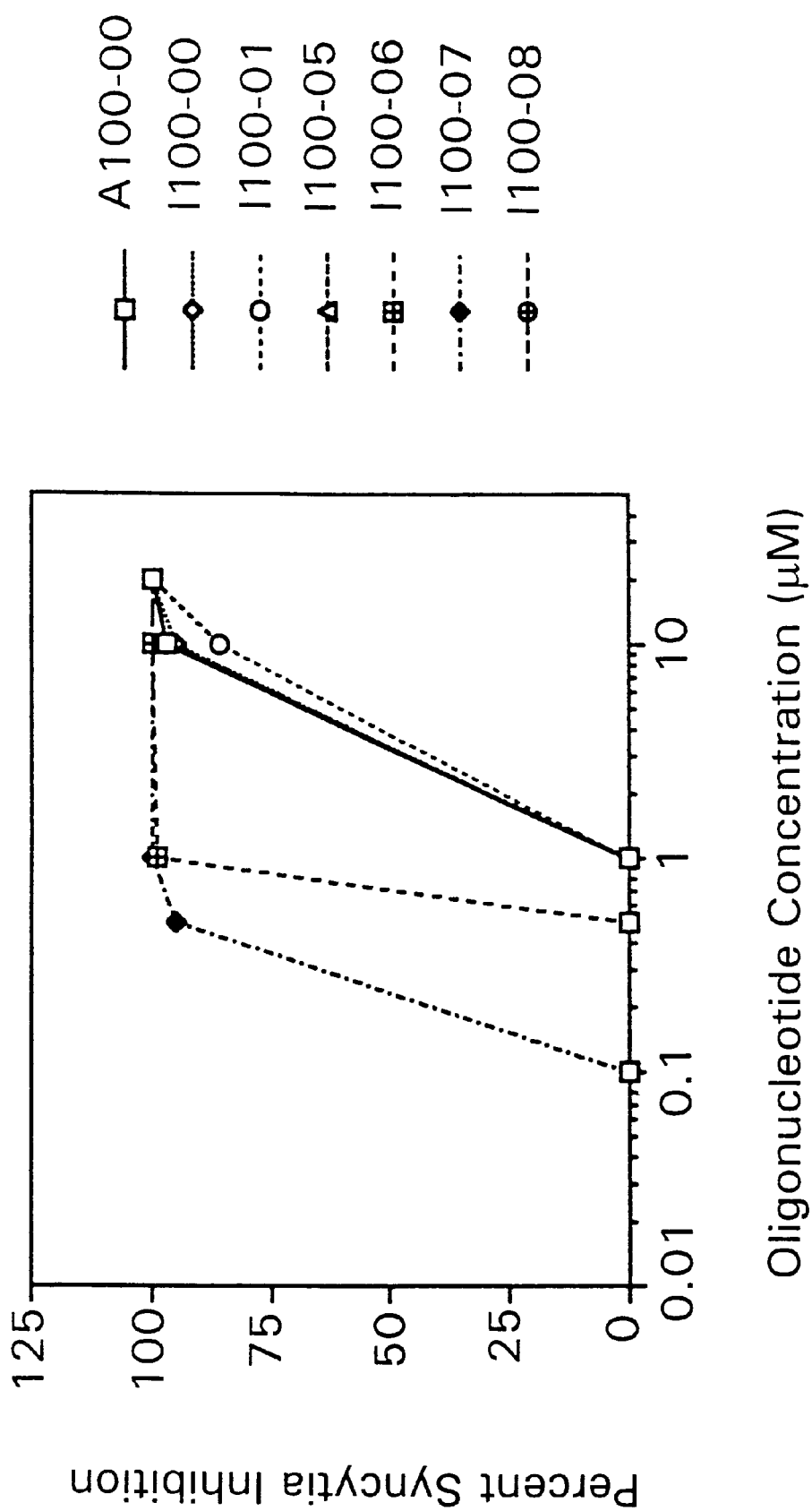
FIG. 6 shows inhibition of HIV-1 induced syncytia formation four days post-infection. SUP T1 cells were infected with HIV-1$_{DV}$ for four hours and then treated with various concentrations of oligonucleotides. Four days post-infection cells were scored for syncytia formation. All assays were performed in quadruplicate and the average values used to plot this graph. The legend to the right of the graph indicates the symbol used for each oligonucleotide tested.
Figure 7:
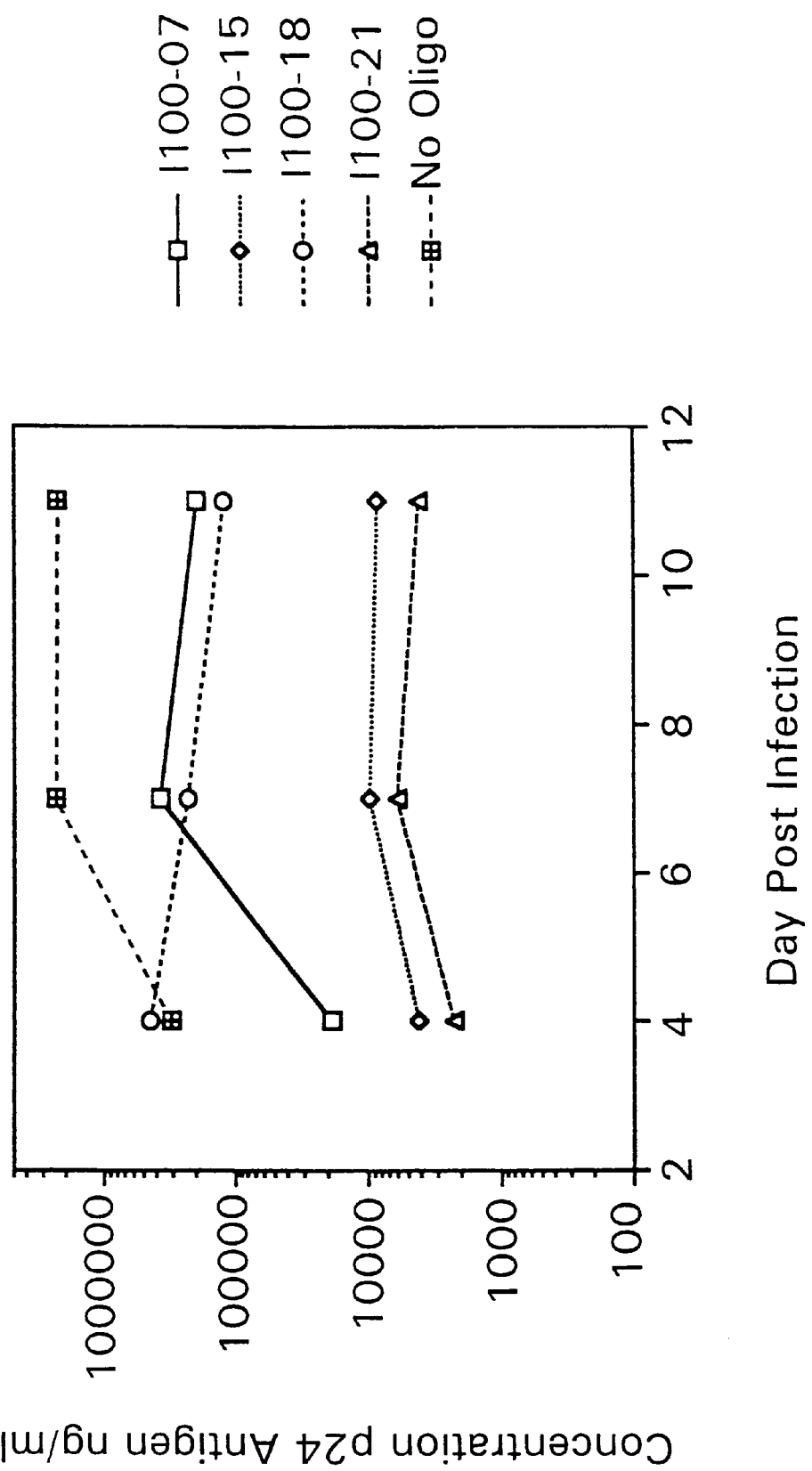
FIG. 7 shows continued suppression of HIV-1 p24 production seven days post removal of oligonucleotide. Four days post-infection with HIV-1$_{DV}$, the media from infected cells treated with oligonucleotides (2.5 $\mu$M) was removed and replaced with fresh media without oligonucleotide. The presence of viral p24 antigen was then assayed 7 and 11-days post infection. All samples were assayed in quadruplicate and the average values used to plot this graph. The legend to the right of the graph indicates the symbol used for each oligonucleotide tested.
Figure 8:
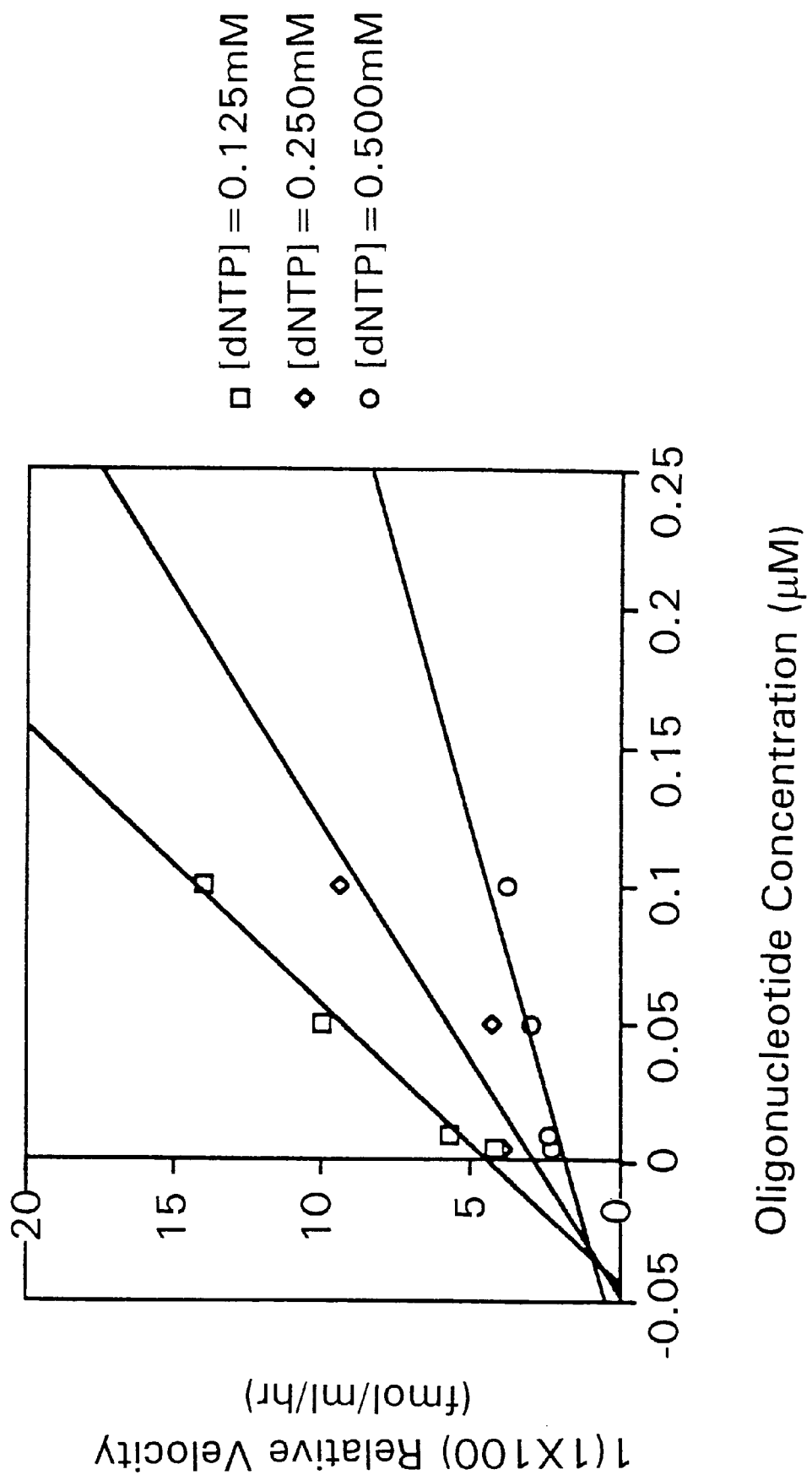
FIG. 8 shows a Dixon Plot of random oligonucleotide 1232 (SEQ. ID. NO. 41) obtained from kinetic analysis of inhibition of HIV-RT with respect to dNTP. The inhibition constant $K_i$ was determined by simultaneously varying dNTP (without dATP) concentrations at the same time as inhibitor (oligonucleotide 1232). The $K_i$ determination was performed at 0.125 mM, 0.25 mM and 0.5 mM dNTP concentrations with constant Primer-Template concentration of 0.2 pM. HIV-RT was used at 1 unit in each reaction. The reported values are the result of simultaneous independent duplicates determinations.

The I100-51 (FMLV2ap), attenuated full length transcription directed by either the T7 or T3 polymerases (FIG. 5a). As can be seen in FIG. 1, full length transcripts directed by the T7 promoter would be 131 bases long while full length transcripts directed by the T3 promoter would be 171 bases long (position of the Dde I site relative to the mRNA start site). The sequence isomer of I100-51 (I100-01=FMLV2p), designed parallel to the target strand was also capable of significantly inhibiting transcription from the T7 promoter (FIG. 5b). However, only the anti-parallel triple helix forming oligonucleotide FMLV2ap inhibited via attenuation of transcription as can be seen in the build up of a truncated transcript in the reaction mix (FIG. 5C). The truncated transcript analyzed in FIG. 5C was approximately 63 bases long and matched the predicted size fragment when p275A was used as a template (T7 promoter). G101-50 (53% G) inhibited T7, but not T3 directed, transcription by a mechanism other than attenuation (FIG. 5A) since no truncated transcripts were observed when this oligonucleotide was used alone. I100-11 (26% G) increased the level of specific transcripts directed by the T7 promoter (FIG. 4b).

In experiments designed to monitor inhibition of transcription initiation of the HSV-1 IE175 promoter, using oligonucleotides, both specific and control G-Rich oligonucleotides were capable of inhibiting eukaryotic transcription when a HeLa cell extract system was used. The oligonucleotides used were B133-54; B133-55 and B107-51 as specific inhibitors via potential triple helix mechanism of action and G101-50 and I100-11 as the low G-content control oligonucleotides.

The present invention demonstrates anti-viral activity in tissue culture assays for several G-Rich oligonucleotides against HSV-2, HIV-1, HCMV and FMLV. In addition, G-Rich oligonucleotides specifically inhibited the bacterial RNA polymerase enzymes T7 and T3, the FMLV and HIV-1 reverse transcriptase enzyme and eukaryotic RNA polymerase.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned as well as those inherent therein. The oligonucleotides, compounds, methods, procedures and techniques described herein are presently representative of preferred embodiments, are intended to be exemplary and are not intended as limitations on the scope. Changes therein and other uses will occur to those skilled in the art which are encompassed within the spirit of the invention or defined by the scope of the appended claims.

What is claimed is:

1. An oligonucleotide containing at least about 40% guanosine residues and at least two runs of at least two guanosine nucleotides selected from the group consisting of SEQ ID NOS 2–27, 29 and 31–39;

optionally modified at the 3' terminus by attachment of a substituent moiety selected from the group consisting of propylamine, polyamine, poly-L-lysine and cholesterol;

optionally modified at the 5'-terminus by attachment of a substituent moiety selected from the group consisting of propylamine, polyamine, poly-L-lysine and cholesterol; and optionally modified by replacement of at least one phosphodiester moiety with a phosphorothioate moiety.

2. The oligonucleotide of claim 1, said oligonucleotide containing a chemical modification at the 3' terminus with a moiety selected from the group consisting of propylamine, polyamine, poly-L-lysine and cholesterol.

3. The oligonucleotide of claim 1, said oligonucleotide containing a chemical modification at the 5' terminus with a moiety selected from the group consisting of propylamine, polyamine, poly-L-lysine and cholesterol.

4. The oligonucleotide of claim 1, said oligonucleotide containing at least one phosphorothioate linkage.

5. An oligonucleotide containing at least about 40% guanosine residues and at least two runs of at least two guanosine nucleotides selected from the group consisting of SEQ ID NOS 46–52;

optionally modified at the 3' terminus by attachment of a substituent moiety selected from the group consisting of propylamine, polyamine, poly-L-lysine and cholesterol;

optionally modified at the 5'-terminus by attachment of a substituent moiety selected from the group consisting of propylamine, polyamine, poly-L-lysine and cholesterol; and optionally modified by replacement of at least one phosphodiester moiety with a phosphorothioate moiety.

6. The oligonucleotide of claim 5, said oligonucleotide containing a chemical modification at the 3' terminus with a moiety selected from the group consisting of propylamine, polyamine, poly-L-lysine and cholesterol.

7. The oligonucleotide of claim 5, said oligonucleotide containing a chemical modification at the 5' terminus with a moiety selected from the group consisting of propylamine, polyamine, poly-L-lysine and cholesterol.

8. The oligonucleotide of claim 5, said oligonucleotide containing at least one phosphorothioate linkage.

9. An oligonucleotide comprising at least about 40% guanosine nucleotides and at least two runs of at least two guanosine nucleotides selected from the group consisting of SEQ ID NOS 2–27, 29, 31–39 and 46–52, said oligonucleotide further comprising a chemical modification at the 3' terminus with a moiety selected from the group consisting of propylamine, polyamine, poly-L-lysine and cholesterol.

10. The oligonucleotide of claim 9, said oligonucleotide further comprising at least one phosphorothioate linkage.

11. An oligonucleotide comprising at least about 40% guanosine nucleotides and at least two runs of at least two guanosine nucleotides selected from the group consisting of SEQ ID NOS 2–27, 29, 31–39 and 46–52, said oligonucleotide further comprising a chemical modification at the 5' terminus with a moiety selected from the group consisting of propylamine, polyamine, poly-L-lysine and cholesterol.

12. The oligonucleotide of claim 11, said oligonucleotide further comprising a chemical modification at the 3' terminus with a moiety selected from the group consisting of propylamine, polyamine, poly-L-lysine and cholesterol.

13. The oligonucleotide of claim 11, said oligonucleotide further comprising at least one phosphorothioate linkage.

14. An oligonucleotide comprising at least about 40% guanosine nucleotides and at least two runs of at least two guanosine nucleotides selected from the group consisting of SEQ ID NOS 2–27, 29, 31–39 and 46–52, said oligonucleotide further comprising at least one phosphorothioate linkage.

15. An oligonucleotide selected from the group consisting of SEQ ID NOS 2–27, 29 and 31–39.

16. An oligonucleotide selected from the group consisting of SEQ ID NOS 46–52.

17. An oligonucleotide having the sequence of any one oligonucleotide defined in claim 15 which additionally contains a chemical modification at the 3' terminus by attachment of a moiety selected from the group consisting of propylamine, polyamine, poly-L-lysine and cholesterol.

18. An oligonucleotide having the sequence of any one oligonucleotide defined in claim 15, said oligonucleotide containing a chemical modification at the 5' terminus with a moiety selected from the group consisting of propylamine, polyamine, poly-L-lysine and cholesterol.

19. An oligonucleotide having the sequence of any one oligonucleotide defined in claim 15, said oligonucleotide containing at least one phosphorothioate linkage.

20. An oligonucleotide having the sequence of any one oligonucleotide defined in claim 16 which additionally contains a chemical modification at the 3' terminus by attachment of a moiety selected from the group consisting of propylamine, polyamine, poly-L-lysine and cholesterol.

21. An oligonucleotide having the sequence of any one oligonucleotide defined in claim or 16, oligonucleotide containing a chemical modification at the 5' terminus with a moiety selected from the group consisting of propylamine, polyamine, poly-L-lysine and cholesterol.

22. An oligonucleotide having the sequence of any one oligonucleotide defined in claim 16, said oligonucleotide containing at least one phosphorothioate linkage.

* * * * *

SEQUENCE LISTING (1) GENERAL INFORMATION:

(iii) NUMBER OF SEQUENCES: 52

(2) INFORMATION FOR SEQ ID NO:1:

(i) SEQUENCE CHARACTERISTICS:
      (A) LENGTH: 38 base pairs
      (B) TYPE: nucleic acid
      (C) STRANDEDNESS: single (D) TOPOLOGY: linear (ii) MOLECULE TYPE: DNA (genomic)

(ix) FEATURE:
        (A) NAME/KEY: misc_feature
        (B) LOCATION: 38
        (D) OTHER INFORMATION: /note= "Amine moity
            attached to 3' end"

(xi) SEQUENCE DESCRIPTION: SEQ ID NO:1:

TGGGTGGGGT GGGGTGGGGG GGTGTGGGGT GTGGGGTG                                38

(2) INFORMATION FOR SEQ ID NO:2:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

GTGGGGTGTG GGGTGTGGGG GGGTGGGGTG GGGTGGGT                                38

(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GGGTGGGTGG GTGGGTGG                                                      18

(2) INFORMATION FOR SEQ ID NO:4:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

GGTGGTGGGG GGGGGTGGGG TGGTGGTGGG GGTGTTGG                                38

(2) INFORMATION FOR SEQ ID NO:5:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GTGGTGGTGG TGTTGGTGGT GGTTTGGGGG GTGGGG                                  36

(2) INFORMATION FOR SEQ ID NO:6:

(i) SEQUENCE CHARACTERISTICS:
        (A) LENGTH: 36 base pairs

```
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GTGGTTGGTG GTGGTGTGTG GGTTTGGGGT GGGGGG                                  36

(2) INFORMATION FOR SEQ ID NO:7:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 36
        (D) OTHER INFORMATION: /note= "phosphorothioate
            backbone"

(xi) SEQUENCE DESCRIPTION: SEQ ID NO:7:

GTGGTGGTGG TGTTGGTGGT GGTTTGGGGG GTGGGG                                  36

(2) INFORMATION FOR SEQ ID NO:8:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 36
        (D) OTHER INFORMATION: /note= "phosphorothioate
            backbone"

(xi) SEQUENCE DESCRIPTION: SEQ ID NO:8:

GTGGTTGGTG GTGGTGTGTG GGTTTGGGGT GGGGGG                                  36

(2) INFORMATION FOR SEQ ID NO:9:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GGTGGGGTGG TGGTGGTTGG GGGGGGGGGG T                                       31

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:
```

GGTGGTTGGG GGGTGGGGGG G                                       21

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

GGGTGGGGTG GTGGGTGGGG G                                       21

(2) INFORMATION FOR SEQ ID NO:12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

GGTGGGTGGT TTGTGTGGTT GGTGGGTTTT                              30

(2) INFORMATION FOR SEQ ID NO:13:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GGGGGGGGGG TGTGGGGGGG GGTTGTGGTG G                            31

(2) INFORMATION FOR SEQ ID NO:14:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

GGTGGGTGGG TTGGGGGGTG GGTGGGG                                 27

(2) INFORMATION FOR SEQ ID NO:15:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

TGGGGTTTGG GTGGGGGGTT GGGTGGTTG                               29

(2) INFORMATION FOR SEQ ID NO:16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

GGGTGGTGGT GTTGGTGTTG TGTG                                              24

(2) INFORMATION FOR SEQ ID NO:17:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

GGTGGGGGGG TTGGTGTGTT TG                                                22

(2) INFORMATION FOR SEQ ID NO:18:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

GTGTGGGGGG GTGGGGTGGG GTGGGT                                            26

(2) INFORMATION FOR SEQ ID NO:19:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

GGGTGGGTGG GTGGGTGGGT GGGTGG                                            26

(2) INFORMATION FOR SEQ ID NO:20:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 26
        (D) OTHER INFORMATION: /note= "Amine moity
            attached to 3' end"

(xi) SEQUENCE DESCRIPTION: SEQ ID NO:20:

GTTGGGGGTT GTTGGTGGGG TGGTGG                                            26

(2) INFORMATION FOR SEQ ID NO:21:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 45
        (D) OTHER INFORMATION: /note= "Amine moity
            attached to 3' end"

(xi) SEQUENCE DESCRIPTION: SEQ ID NO:21:

TGGTGGGTGT GTGGGGGGTG TTGGGGGTTG TTGGTGGGGT GGTGG                    45

(2) INFORMATION FOR SEQ ID NO:22:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 45
        (D) OTHER INFORMATION: /note= "cholesterol moity
            attached to 3' end"

(xi) SEQUENCE DESCRIPTION: SEQ ID NO:22:

TGGTGGGTGT GTGGGGGGTG TTGGGGGTTG TTGGTGGGGT GGTGG                    45

(2) INFORMATION FOR SEQ ID NO:23:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 45
        (D) OTHER INFORMATION: /note= "cholesterol moity
            attached to 3' end"

(xi) SEQUENCE DESCRIPTION: SEQ ID NO:23:

GTGGTGGGTG GGTGGGTGGT GGGTGGTGGT TGTGGGTGGG TGGTG                    45

(2) INFORMATION FOR SEQ ID NO:24:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 45
        (D) OTHER INFORMATION: /note= "Amine moity

```
          attached to 3' end"

(xi) SEQUENCE DESCRIPTION: SEQ ID NO:24:

GTGGTGGGTG GGTGGGTGGT GGGTGGTGGT TGTGGGTGGG TGGTG                45

(2) INFORMATION FOR SEQ ID NO:25:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: misc_feature
      (B) LOCATION: 26
      (D) OTHER INFORMATION: /note= "cholesterol moity
          attached to 3' end"

(xi) SEQUENCE DESCRIPTION: SEQ ID NO:25:

GTTGGGGGTT GTTGGTGGGG TGGTGG                                     26

(2) INFORMATION FOR SEQ ID NO:26:

(i) SEQUENCE CHARACTERISTICS:
      (A) LENGTH: 45 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: misc_feature
      (B) LOCATION: 45
      (D) OTHER INFORMATION: /note= "Amine moity
          attached to 3' end"

(xi) SEQUENCE DESCRIPTION: SEQ ID NO:26:

GATCCATGTC AGTGACACTG CGTAGATCCG ATGATCCAGT CGATG                45

(2) INFORMATION FOR SEQ ID NO:27:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: misc_feature
      (B) LOCATION: 26
      (D) OTHER INFORMATION: /note= "phosphorothioate
          backbone and amine moity attached to
          backbone"

(xi) SEQUENCE DESCRIPTION: SEQ ID NO:27:

GTTGGGGGTT GTTGGTGGGG TGGTGG                                     26

(2) INFORMATION FOR SEQ ID NO:28:

(i) SEQUENCE CHARACTERISTICS:
      (A) LENGTH: 26 base pairs
      (B) TYPE: nucleic acid
      (C) STRANDEDNESS: single
      (D) TOPOLOGY: linear
```

```
        (ii) MOLECULE TYPE: DNA (genomic)

(xi) SEQUENCE DESCRIPTION: SEQ ID NO:28:

GGTGGTGGGG TGGTTGTTGG GGGTTG                                             26

(2) INFORMATION FOR SEQ ID NO:29:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:29:

GGTGGTGGGG TGGTTGTTGG GGGTTGTTGG GGGTGTGTGG GTGGT                        45

(2) INFORMATION FOR SEQ ID NO:30:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:30:

GGGTGGTTGG GTGGTTGG                                                      18

(2) INFORMATION FOR SEQ ID NO:31:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_feature
            (B) LOCATION: 18
            (D) OTHER INFORMATION: /note= "Amine moity
                attached to 3' end"

(xi) SEQUENCE DESCRIPTION: SEQ ID NO:31:

GGGTGGGTGG GTGGGTGG                                                      18

(2) INFORMATION FOR SEQ ID NO:32:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_feature
            (B) LOCATION: 18
            (D) OTHER INFORMATION: /note= "Amine moity
                attached to 3' end and phosphothioate
                backbone"

(xi) SEQUENCE DESCRIPTION: SEQ ID NO:32:

GGGTGGGTGG GTGGGTGG                                                      18
```

(2) INFORMATION FOR SEQ ID NO:33:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 17
        (D) OTHER INFORMATION: /note= "Amine moity
            attached to 3' end"

(xi) SEQUENCE DESCRIPTION: SEQ ID NO:33:

GTGGTGGGTG GGTGGGT                                                17

(2) INFORMATION FOR SEQ ID NO:34:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 27
        (D) OTHER INFORMATION: /note= "Amine moity
            attached to 3' end"

(xi) SEQUENCE DESCRIPTION: SEQ ID NO:34:

GTGGTGGGTG GGTGGGTGGT GGGTGGT                                27

(2) INFORMATION FOR SEQ ID NO:35:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 37
        (D) OTHER INFORMATION: /note= "Amine moity
            attached to 3' end"

(xi) SEQUENCE DESCRIPTION: SEQ ID NO:35:

GTGGTGGGTG GGTGGGTGGT GGGTGGTGGT TGTGGGT                  37

(2) INFORMATION FOR SEQ ID NO:36:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 16
        (D) OTHER INFORMATION: /note= "Amine moity
            attached to 3' end"

(xi) SEQUENCE DESCRIPTION: SEQ ID NO:36:

TTGTGGGTGG GTGGTG                                                        16

(2) INFORMATION FOR SEQ ID NO:37:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_feature
            (B) LOCATION: 29
            (D) OTHER INFORMATION: /note= "Amine moity
                attached to 3' end"

(xi) SEQUENCE DESCRIPTION: SEQ ID NO:37:

TGGTGGGTGG TGGTTGTGGG TGGGTGGTG                                          29

(2) INFORMATION FOR SEQ ID NO:38:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_feature
            (B) LOCATION: 38
            (D) OTHER INFORMATION: /note= "Amine moity
                attached to 3' end"

(xi) SEQUENCE DESCRIPTION: SEQ ID NO:38:

GTGGGTGGGT GGTGGGTGGT GGTTGTGGGT GGGTGGTG                                38

(2) INFORMATION FOR SEQ ID NO:39:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_feature
            (B) LOCATION: 45
            (D) OTHER INFORMATION: /note= "phosphorothioate
                backbone and amine moity attached to 3' end"

(xi) SEQUENCE DESCRIPTION: SEQ ID NO:39:

GTGGTGGGTG GGTGGGTGGT GGGTGGTGGT TGTGGGTGGG TGGTG                        45

(2) INFORMATION FOR SEQ ID NO:40:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

```
    (ix) FEATURE:
        (A) NAME/KEY: misc_feature
        (B) LOCATION: 18
        (D) OTHER INFORMATION: /note= "Amine moity
             attached to 3' end"

(xi) SEQUENCE DESCRIPTION: SEQ ID NO:40:

GATCCATGTC AGTGACAC                                              18

(2) INFORMATION FOR SEQ ID NO:41:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 18
        (D) OTHER INFORMATION: /note= "Amine moity
             attached to 3' end and phosphorothioate
             backbone"

(xi) SEQUENCE DESCRIPTION: SEQ ID NO:41:

GATCCATGTC AGTGACAC                                              18

(2) INFORMATION FOR SEQ ID NO:42:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 18
        (D) OTHER INFORMATION: /note= "Amine moity
             attached to 3' end"

(xi) SEQUENCE DESCRIPTION: SEQ ID NO:42:

CCCCCCCCCC CCCCCCCC                                              18

(2) INFORMATION FOR SEQ ID NO:43:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 18
        (D) OTHER INFORMATION: /note= "Amine moity
             attached to 3' end and phosphorothioate
             backbone"

(xi) SEQUENCE DESCRIPTION: SEQ ID NO:43:

CCCCCCCCCC CCCCCCCC                                              18

(2) INFORMATION FOR SEQ ID NO:44:

(i) SEQUENCE CHARACTERISTICS:
```

```
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:44:

TTCATTTGGG AAACCCTTGG AACCTGACTG ACTGGCCGTC GTTTTAC                47

(2) INFORMATION FOR SEQ ID NO:45:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:45:

GTAAAACGAC GGCCA                                                   15

(2) INFORMATION FOR SEQ ID NO:46:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:46:

GTGGTGGGTG GGTGGGG                                                 17

(2) INFORMATION FOR SEQ ID NO:47:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:47:

GTGGTGGGTG GGTGGG                                                  16

(2) INFORMATION FOR SEQ ID NO:48:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:48:

TGGTGGGTGG GTGGGT                                                  16

(2) INFORMATION FOR SEQ ID NO:49:

(i) SEQUENCE CHARACTERISTICS:
        (A) LENGTH: 13 base pairs
        (B) TYPE: nucleic acid
        (C) STRANDEDNESS: single
        (D) TOPOLOGY: linear
```

-continued

```
        (ii) MOLECULE TYPE: DNA (genomic)

(xi) SEQUENCE DESCRIPTION: SEQ ID NO:49:

GTGGTGGGTG GGT                                                          13

(2) INFORMATION FOR SEQ ID NO:50:

(i) SEQUENCE CHARACTERISTICS:
             (A) LENGTH: 9 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:50:

GTGGTGGGT                                                                9

(2) INFORMATION FOR SEQ ID NO:51:

(i) SEQUENCE CHARACTERISTICS:
             (A) LENGTH: 14 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:51:

GTGGGTGGGT GGGT                                                         14

(2) INFORMATION FOR SEQ ID NO:52:

(i) SEQUENCE CHARACTERISTICS:
             (A) LENGTH: 10 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:52:

GTGGGTGGGT                                                              10
```